(12) United States Patent
Nimura et al.

(10) Patent No.: US 11,351,293 B2
(45) Date of Patent: Jun. 7, 2022

(54) BLOOD PURIFICATION DEVICE AND PRIMING METHOD

(71) Applicant: NIKKISO CO., LTD., Tokyo (JP)

(72) Inventors: Hiroshi Nimura, Makinohara (JP); Yoshimichi Masuda, Makinohara (JP); Masato Fujiwara, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 197 days.

(21) Appl. No.: 16/321,767

(22) PCT Filed: Aug. 7, 2017

(86) PCT No.: PCT/JP2017/028623
§ 371 (c)(1),
(2) Date: Jan. 29, 2019

(87) PCT Pub. No.: WO2018/030353
PCT Pub. Date: Feb. 15, 2018

(65) Prior Publication Data
US 2020/0230311 A1 Jul. 23, 2020

(30) Foreign Application Priority Data
Aug. 9, 2016 (JP) .............................. JP2016-156942

(51) Int. Cl.
*A61M 1/36* (2006.01)
*A61M 1/34* (2006.01)
*A61M 1/16* (2006.01)

(52) U.S. Cl.
CPC .......... *A61M 1/365* (2014.02); *A61M 1/1696* (2013.01); *A61M 1/3434* (2014.02); *A61M 1/3647* (2014.02); *A61M 1/3649* (2014.02)

(58) Field of Classification Search
CPC .. A61M 1/365; A61M 1/3434; A61M 1/3647; A61M 1/3649; A61M 1/1696; A61M 1/36
See application file for complete search history.

(56) References Cited

U.S. PATENT DOCUMENTS 4,619,640 A  10/1986 Potolsky et al.
4,967,173 A  10/1990 Watson
(Continued)

FOREIGN PATENT DOCUMENTS

CN  101641122 A  2/2010
CN  103282062 A  9/2013
(Continued)

OTHER PUBLICATIONS

Nov. 7, 2017 International Search Report issued in International Patent Application No. PCT/JP2017/028625.
(Continued)

*Primary Examiner* — Bradley R Spies
*Assistant Examiner* — Jeannie McDermott
(74) *Attorney, Agent, or Firm* — Oliff PLC

(57) ABSTRACT

A blood purification device used with a blood circuit includes an arterial-side line and a venous-side line attached to a blood purifier to which, at the ends thereof, the arterial-side line and the venous-side line are connected, the blood purification device including: a supply line connected to a supply unit which supplies a priming fluid, and which is capable of being connected to a leading end of the venous-side line; a discharge line connected to a discharge unit which discharges the priming fluid after use, and which is capable of being connected to a leading end of the arterial-side line; and a blood pump which is disposed upon the arterial-side line. By driving the blood pump in a state of the supply line being connected to the venous-side line and the discharge line being connected to the arterial-side line, the blood circuit and the blood purifier are primed.

20 Claims, 14 Drawing Sheets

(56) References Cited

U.S. PATENT DOCUMENTS

| | | |
|---|---|---|
| 5,725,511 A | 3/1998 | Urrutia |
| 5,762,805 A | 6/1998 | Truitt et al. |
| 5,776,345 A | 7/1998 | Truitt et al. |
| 5,947,937 A | 9/1999 | Urrutia et al. |
| 6,402,207 B1 | 6/2002 | Segal et al. |
| 2003/0010717 A1 | 1/2003 | Brugger et al. |
| 2004/0217586 A1 | 11/2004 | Mastropaolo |
| 2005/0230314 A1 | 10/2005 | Kim et al. |
| 2005/0267445 A1 | 12/2005 | Mendels |
| 2006/0100564 A1 | 5/2006 | Sano et al. |
| 2007/0076401 A1 | 4/2007 | Carrez et al. |
| 2008/0228125 A1 | 9/2008 | Brugger et al. |
| 2008/0318456 A1 | 12/2008 | Yow et al. |
| 2009/0076433 A1 | 3/2009 | Folden et al. |
| 2009/0099552 A1 | 4/2009 | Levy et al. |
| 2010/0078385 A1 | 4/2010 | Kawarabata et al. |
| 2013/0303963 A1 | 11/2013 | Breuch et al. |
| 2014/0048460 A1 | 2/2014 | Paolini et al. |
| 2015/0151036 A1* | 6/2015 | Furuhashi ............ A61M 1/3644 210/646 |
| 2016/0250405 A1 | 9/2016 | Kogoshi et al. |
| 2017/0072122 A1 | 3/2017 | Mochizuki |
| 2017/0232180 A1 | 8/2017 | Umeda et al. |
| 2018/0021512 A1 | 1/2018 | Fukuoka et al. |
| 2018/0110914 A1* | 4/2018 | Fujiwara ............ A61M 1/3649 |
| 2019/0117950 A1 | 4/2019 | Carlsson |
| 2019/0184150 A1 | 6/2019 | Nimura et al. |
| 2020/0276381 A1 | 9/2020 | Gutzler et al. |
| 2021/0162124 A1 | 6/2021 | Nakagawa et al. |
| 2021/0187265 A1 | 6/2021 | Schuler |

FOREIGN PATENT DOCUMENTS

| | | |
|---|---|---|
| EP | 2 142 234 B1 | 1/2013 |
| EP | 2197513 B1 | 4/2017 |
| EP | 3 266 496 A2 | 1/2018 |
| JP | H03-105264 A | 5/1991 |
| JP | H06-315530 A | 11/1994 |
| JP | H07-313590 A | 12/1995 |
| JP | 2003-180823 A | 7/2003 |
| JP | 2003-531687 A | 10/2003 |
| JP | 2006-130063 A | 5/2006 |
| JP | 2006-175103 A | 7/2006 |
| JP | 2007-512885 A | 5/2007 |
| JP | 2007-215557 A | 8/2007 |
| JP | 2010-538800 A | 12/2010 |
| JP | 2012-034992 A | 2/2012 |
| JP | 5399218 B2 | 1/2014 |
| JP | 2015-213642 A | 12/2015 |
| JP | 2016-000367 A | 1/2016 |
| JP | 2020-048948 A | 4/2020 |
| WO | 2005/118485 A1 | 12/2005 |
| WO | 2010/042666 A2 | 4/2010 |
| WO | 2012/085644 A1 | 6/2012 |
| WO | 2015/068833 A1 | 5/2015 |
| WO | 2016/067946 A1 | 5/2016 |
| WO | 2018/030354 A1 | 2/2018 |

OTHER PUBLICATIONS

Feb. 11, 2019 U.S. Appl. No. 16/324,740 in the name of Hiroshi Nimura et al.
Sep. 3, 2020 Office Action issued in Chinese Patent Application No. 201780047017.4.
Jan. 30, 2020 Extended European Search Report Issued in European Patent Application No. 17839424.3.
Nov. 21, 2019 Extended Search Report issued in European Patent Application No. 19189412.0.
Jun. 27, 2019 Extended Search Report issued in European Patent Application No. 17839425.0.
Oct. 2017 Search Report issued in International Patent Application No. PCT/JP2017/028623.
May 25, 2021 Office Action issued in Japanese Patent Application No. 2018-533462.
May 7, 2021 Office Action issued in Chinese Patent Application No. 201780047017.4.
Jan. 11, 2022 Office Action issued in U.S. Appl. No. 16/324,740.
Dec. 14, 2021 Office Action issued in Japanese Patent Application No. 2018-533462.

* cited by examiner

BLOOD PURIFICATION DEVICE AND PRIMING METHOD

TECHNICAL FIELD

The present invention relates to a blood purification device used with a blood circuit, which includes an arterial side line and a venous side line, and a blood purifier, to both ends of which the arterial side line and the venous side line are connected, attached thereto, and a priming method for the blood circuit and the blood purifier.

BACKGROUND

There has been known a blood purification device for performing a blood purifying method for purifying, outside a body, blood drawn from a patient and thereafter returning the blood into the body. In the blood purification device, for example, a pump for delivering blood, dialysis fluid, and the like, a valve for restricting a flow of fluid, a supplying part or a discharging part for supplying or discharging the dialysis fluid, replenisher, and the like are provided. In the blood purifying method, a blood circuit in which blood flows and a blood purifier that purifies the blood are necessary. Note that the blood circuit includes at least an arterial side line in which the blood drawn from the patient flows and a venous side line in which the blood after being purified by the blood purifier flows. The blood circuit and the blood purifier are disposable members discarded and replaced at each time of use, from the viewpoint of hygiene. Therefore, an operator sets the blood circuit and the blood purifier in the blood purification device at each time of use.

Usually, when such a blood purification device is used to perform blood purification, processing called "priming" for supplying priming fluid to the blood circuit and the blood purifier and removing air on the insides of the blood circuit and the blood purifier is performed in advance. Patent Literatures 1 to 3 disclose dialyzing devices that can relatively easily perform such priming processing.

In the dialyzing devices, a dialyzer is used as the blood purifier. In this case, the blood purification device includes a lead-in line for leading dialysis fluid into the dialyzer and a lead-out line for leading out the dialysis fluid from the dialyzer. The dialyzing devices disclosed in Patent Literatures 1 and 3 feed, when executing the priming, dialysis fluid functioning as priming fluid from the lead-in line into the dialyzer and the blood circuit. In the dialyzing device disclosed in Patent Literature 2, a new line branching from the lead-in line and connected midway in the arterial side line is provided. When the priming is executed, the dialysis fluid functioning as the priming fluid is fed into the blood circuit via the new line.

CITATION LIST

Patent Literature

Patent Literature 1: JP 2003-180823 A
Patent Literature 2: JP 5399218 B
Patent Literature 3: EP Patent No. 2142234

SUMMARY

Technical Problem

However, the techniques of Patent Literatures 1 and 2 have a problem in that a branch line unnecessary for treatment is included in the blood circuit discarded and replaced at each time of use. That is, as explained above, the blood circuit and the blood purifier are the disposable members replaced and discarded at each time of use, and are set in the blood purification device at each time of use. In the techniques of Patent Literatures 1 and 2, the branch line used for only the priming, and unnecessary for treatment, is included in the blood circuit (the disposable member). Such a branch line unnecessary for treatment easily causes misunderstanding and confusion of the operator and makes setting work of the blood circuit difficult. The branch line unnecessary for treatment easily hinders work.

In the technique of Patent Literature 3, the branch line used only for the priming and unnecessary for treatment is not provided in the blood circuit. Therefore, according to the technique of Patent Literature 3, misunderstanding and confusion of the operator can be reduced and setting work for the blood circuit can be simplified. However, in the techniques of Patent Literatures 1 and 3, there is a problem in that air in the dialyzer cannot be sufficiently eliminated. That is, in Patent Literatures 1 and 3, as explained above, the dialysis fluid functioning as the priming fluid is fed in the order of the lead-in line, the dialyzer, and the blood circuit. In this case, the dialysis fluid changes to a state of "back filtration" in which the dialysis fluid flows from the outer side to the inner side of a hollow fiber membrane provided in the dialyzer. When the dialysis fluid is back-filtered, the dialysis fluid flows in a concentrated state to only a part to which dialysis fluid easily flows in the hollow fiber membrane. As a result, a part to which the dialysis fluid does not flow at all is formed in the hollow fiber membrane. Air locks in which the air remains are likely to occur.

That is, there has been no blood purification device that can sufficiently eliminate air from a blood purifier and a blood circuit while being easy to handle. Therefore, an object of the present invention is to provide a blood purification device and a priming method that can sufficiently eliminate air while being easy to handle.

Solution to Problem

A blood purification device of the present invention is a blood purification device used with a blood circuit, which includes an arterial side line and a venous side line, and a blood purifier, to both ends of which the arterial side line and the venous side line are connected, attached thereto, the blood purification device including: a supply line connected to a supplying part that supplies priming fluid and that is connectable to a distal end of the venous side line; a discharge line connected to a discharging part that discharges the priming fluid after use and that is connectable to a distal end of the arterial side line; and a blood pump provided midway in the arterial side line. In a state in which the supply line and the venous side line are connected and the discharge line and the arterial side line are connected, the blood purification device drives the blood pump to prime the blood circuit and the blood purifier.

In a preferred aspect, when the blood circuit and the blood purifier are primed, the blood pump is reversely driven to deliver fluid in a direction opposite to a direction during execution of a blood purifying method.

In another preferred aspect, the blood purifier is a dialyzer, the supplying part is a dialysis fluid supply device that supplies dialysis fluid to the dialyzer, and the supply line is a line branching midway in a lead-in line that connects the dialysis fluid supply device and the dialyzer.

In another preferred aspect, the blood purifier is a dialyzer, the discharging part is a dialysis fluid discharge device that discharges dialysis fluid from the dialyzer, and the discharge line is a line that joins midway in a lead-out line that connects the dialysis fluid supply device and the dialyzer.

In this case, it is desirable that the blood purification device further includes: a lead-in pump that is provided midway in the lead-in line and sends fluid supplied from the dialysis fluid supply device to the dialyzer; a lead-out pump that is provided midway in the lead-out line and sends the fluid discharged from the dialyzer to the dialysis fluid discharge device; and a switching mechanism that switches a supply destination of the fluid supplied from the dialysis fluid supply device to the supply line or the dialyzer, and in the priming, the blood purification device executes first priming processing for driving the blood pump in a state in which the supply destination of the fluid is switched to the supply line and second priming processing for driving the lead-in pump and the lead-out pump in a state in which the supply destination of the fluid is switched to the blood purifier. It is desirable that the priming fluid is dialysis fluid.

In this case, it is desirable that, in the second priming processing, the lead-in pump and the lead-out pump are normally driven to deliver the fluid in the sane direction as a direction during execution of a blood purifying method.

In another preferred aspect, the supplying part is a priming fluid container filled with the priming fluid or a line connected to a supply source of the priming fluid provided on the outside of the blood purification device.

In another preferred aspect, the discharging part is a discharge fluid container filled with used priming fluid or a line connected to a discarding part of the priming fluid provided on the outside of the blood purification device.

In another preferred aspect, the blood circuit further includes a replenishment fluid line that is connected midway in at least one line of the venous side line and the arterial side line and guides fluid to be replenished to the at least one line. The blood purification device further includes a replenishment fluid pump that is provided midway in the at least one line and sends the fluid to be replenished to the at least one line. The blood purification device drives the replenishment fluid pump to prime the replenishment fluid line.

A priming method, which is another aspect of the present invention, is a priming method for discharging air from a blood circuit including an arterial side line and a venous side line and a blood purifier, to both ends of which the arterial side line and the venous side line are connected, the priming method including: a step of connecting, to the venous side line, a supply line connected to a supplying part that supplies priming fluid and that is connectable to a distal end of the venous side line; a step of connecting, to the arterial side line, a discharge line connected to a discharging part that discharges the priming fluid after use and that is connectable to a distal end of the arterial side line; and a step of driving a blood pump provided midway in the arterial side line and feeding the priming fluid to the blood circuit and the blood purifier.

A blood purification device, which is another aspect of the present invention, is a blood purification device used with a blood circuit, which includes an arterial side line and a venous side line, and a blood purifier, to both ends of which the arterial side line and the venous side line are connected, attached thereto, the blood purification device including: a blood pump provided midway in the arterial side line; and a control part that controls at least driving of the blood pump. In a state in which a supplying part that supplies priming fluid and the venous side line are connected, and a discharging part from which the priming fluid after use is discharged and the arterial side line are connected, when receiving instruction for priming execution, the control part drives the blood pump and executes first priming processing for priming the blood circuit and the blood purifier.

In a preferred aspect, in the first priming processing, the control part reversely drives the blood pump to deliver fluid in the direction opposite to a direction during execution of a blood purifying method.

In another preferred aspect, the blood purification device further includes: a second discharging part; a lead-in line that connects the second discharging part and the blood purifier; a lead-out line that connects the second discharging part and the blood purifier; a lead-in pump provided midway in the lead-in line; and a lead-out pump provided midway in the lead-out line. After the first priming processing, the control part drives the lead-in pump and the lead-out pump and executes second priming processing for feeding the priming fluid to the lead-in line and the lead-out line.

In this case, in the second priming processing, the control part may normally drive the lead-in pump and the lead-out pump to deliver fluid in the same direction as a direction during execution of a blood purifying method.

In this case, in the second priming processing, the control part may normally drive the lead-out pump to deliver fluid in the same direction as a direction during execution of a blood purifying method and reversely drive the lead-in pump to deliver the fluid in a direction opposite to the direction during the execution of the blood purifying method.

Advantageous Effects of Invention

According to the present invention, since the supply line and the discharge line are connected to the distal ends of the venous side line and the arterial side line, it is unnecessary to provide a branch line that is not necessary for treatment on the blood circuit side. According to the present invention, since the priming fluid flows in the axial direction in the blood purifier, back filtration does not occur. The air can be more reliably eliminated. Therefore, according to the present invention, it is possible to sufficiently eliminate the air while allowing easy handling.

DESCRIPTION OF EMBODIMENTS

Embodiments of the present invention are explained below with reference to the drawings. In the following explanation, "normal driving" of a pump indicates a driving direction of the pump in executing a blood purifying method.

Figure 1:
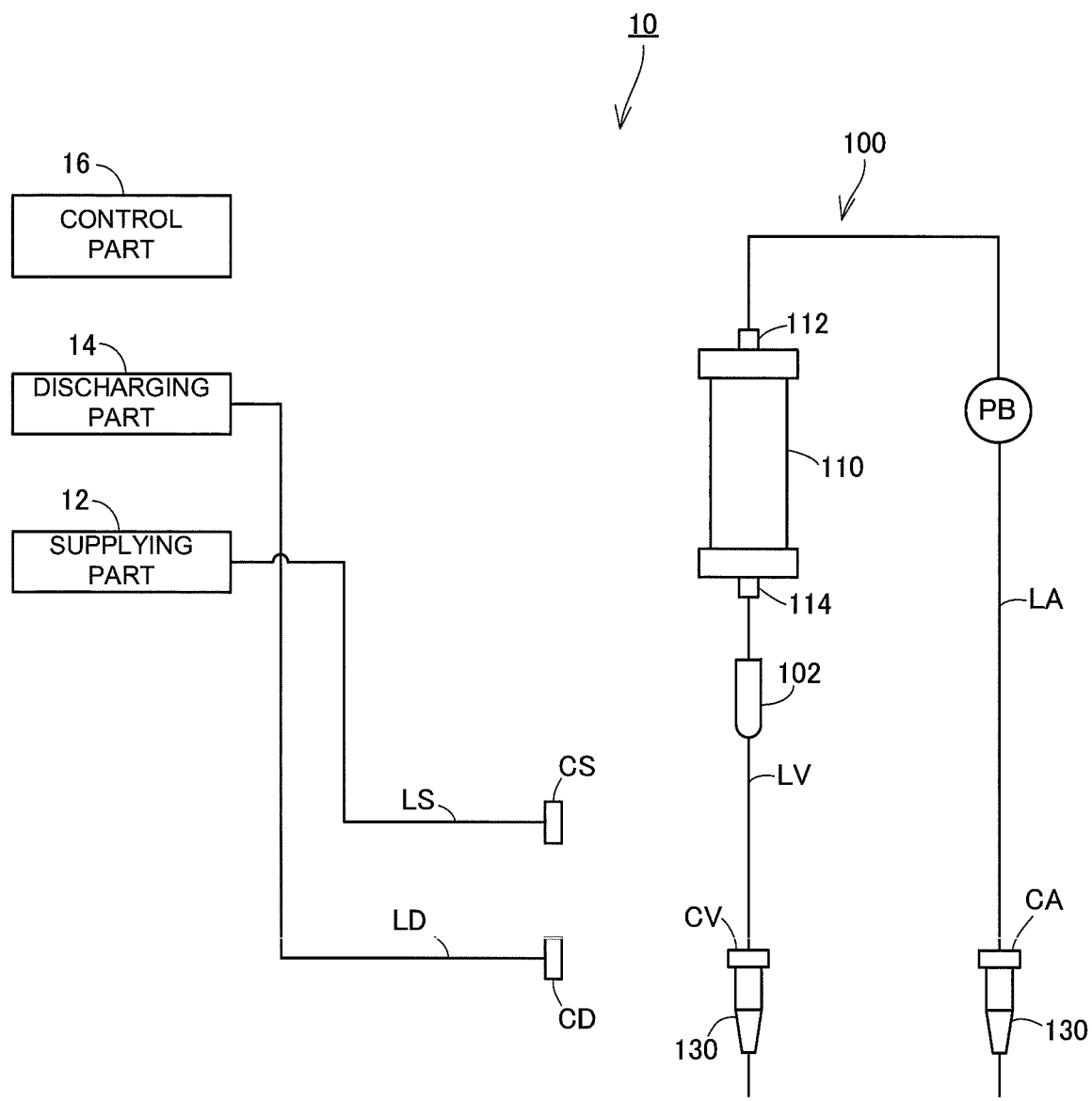
FIG. 1 is a diagram showing the configuration of a blood purification device in a first embodiment of the present invention.
Figure 2:
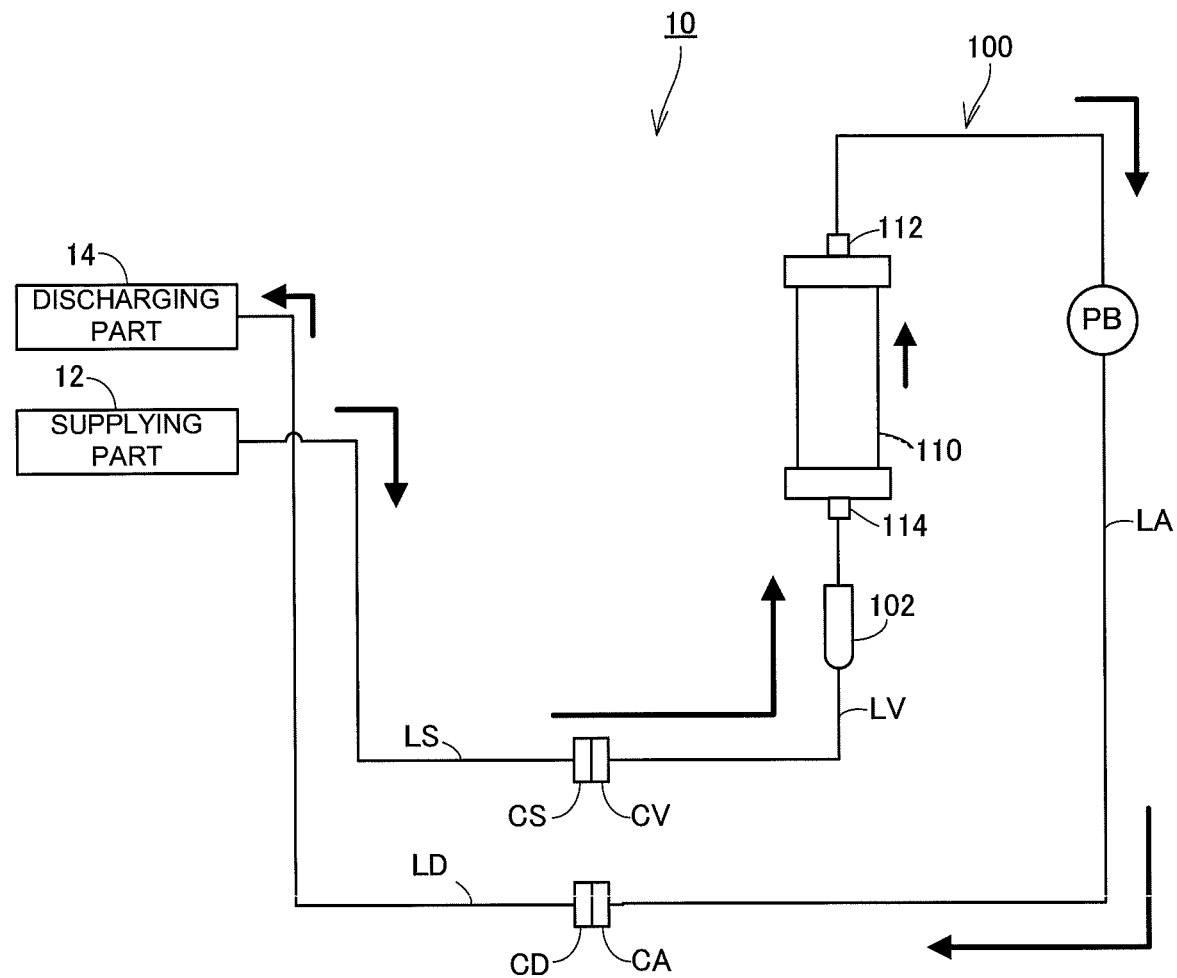
FIG. 2 is a diagram showing the configuration in performing priming processing in the blood purification device in the first embodiment.

FIG. 1 is a diagram showing the configuration of a blood purification device 10 in a basic embodiment of the present invention. FIG. 2 is a diagram showing the configuration of the blood purification device 10 in performing priming processing. Note that in this application, "priming" means cleaning and removing very small dust, a protective agent of a membrane, filling fluid, and air in a blood purifier (e.g., a dialyzer) and a blood circuit, and setting the blood purifier and the blood circuit in a state in which treatment can be started. This blood purification device 10 is a device for executing a blood purifying method for purifying blood drawn from a patient on the outside of a body and thereafter returning the blood into the body. In FIG. 1 and FIG. 2, only basic components are shown. However, other components may be added to the blood purification device 10 as appropriate, according to a type of a blood purifying method to be executed. Examples of the blood purifying method executed by the blood purification device 10 include hemodialysis, hemofiltration, diafiltration, direct blood perfusion, and simple plasmapheresis. Examples of the components that can be added to the blood purification device 10 shown in FIG. 1 and FIG. 2 include a dialysis fluid supplying and discharging device that supplies and discharges dialysis fluid, a pump for delivering the dialysis fluid, and a line and a pump for supplying replenishment fluid for supplementing components removed by blood purification.

In the following explanation, a basic configuration shown in FIG. 1 and FIG. 2 is explained. This blood purification device 10 circulates, outside of a body, blood drawn from a patient, and is used in a state in which a consumable unit is set. The consumable unit includes a blood purifier 110 and a blood circuit 100. The blood purifier 110 is a device that purifies blood drawn from a patient. As this blood purifier 110, for example, a dialyzer suitable for hemodialysis and diafiltration, a blood filter (a hemofilter) suitable for hemofiltration, a blood purification column suitable for direct blood perfusion, and a plasma separator suitable for simple plasmapheresis can be used. The blood purifier 110 is formed in a substantially cylindrical shape. Purifying members for purifying blood, for example, a hollow fiber membrane and an absorber, are housed therein. A blood inlet 112 and a blood outlet 114 are formed at both ends of the blood purifier 110 in the axial direction. The blood drawn from the patient is led into the blood purifier 110 from the blood inlet 112 and purified by the purifying member provided on the inside of the blood purifier 110, and thereafter returned to the patient from the blood outlet 114.

The blood circuit 100 is a fluid circuit in which blood and fluid (e.g., replenishment fluid or fresh frozen plasma) are supplied to the blood flow. The blood circuit 100 is discarded and replaced at each time of use. In the example shown in FIG. 1 and FIG. 2, the blood circuit 100 includes an arterial side line LA in which blood drawn from a patient flows, a venous side line LV in which purified blood flows, and an air trap chamber 102 that temporarily stores the blood in order to eliminate air bubbles in the blood. Both of the arterial side line LA and the venous side line LV are configured by flexible tubes. One end of the arterial side line LA is connected to the blood inlet 112 of the blood purifier 110. One end of the venous side line LV is connected to the blood outlet 114 of the blood purifier 110. An arterial side connector CA, which is a shunt connector, is provided at the distal end (an end portion on an opposite side to the blood purifier 110) of the arterial side line LA. A venous side connector CV, which is a shunt connector, is provided at the distal end of the venous side line LV. Puncture needles 130 can be detachably connected to the two connectors CA and CV. The puncture needles 130 are pierced into the patient to form an extracorporeal circulation route of blood. Note that in this specification, the side of a puncture needle for removing (sampling) blood is referred to as "arterial side" and a side of a puncture needle for returning the blood is referred to as "venous side". Therefore, the "arterial side" and the "venous side" are not decided according to whether a puncture target blood vessel is an artery or a vein.

The air trap chamber 102 is a container that temporarily stores blood. By temporarily storing blood in the air trap chamber 102, air bubbles included in the blood are captured without flowing further downstream than the air trap chamber 102. In the example shown in FIG. 1 and FIG. 2, the air trap chamber 102 is only provided midway in the venous side line LV. However, the air trap chamber 102 may be provided midway in the arterial side line LA in addition to or instead of being provided midway in the venous side line LV. A pressure sensor for detecting pressure may be connected to the air trap chamber 102. The configuration of the blood circuit 100 explained above is an example and may be changed as appropriate. For example, the blood circuit 100 may further include a replenishment fluid line in which replenishment fluid for supplementing components lost in the blood purification and fresh frozen plasma flow.

The configuration of the blood purification device 10 will be explained. The blood purification device 10 includes a blood pump PB for delivering blood. As shown in FIG. 1 and FIG. 2, the blood pump PB is provided midway in the arterial side line LA. The blood pump PB is normally driven, whereby blood is sent to the downstream side (the blood purifier 110 side). As explained in detail below, during priming processing, the blood pump PB is reversely driven to play a role of feeding priming fluid. The configuration of the blood pump PB is not particularly limited. However, in this embodiment, the blood pump PB is a squeezing-type tube pump. The blood pump PB squeezes the arterial side line LA formed by the flexible tube to deliver the blood, the priming fluid, and the like.

Prior to execution of blood purification, the blood purification device 10 also performs priming processing for filling the insides of the blood purifier 110 and the blood circuit 100 with fluid. In order to perform the priming processing, the blood purification device 10 further includes a supplying part 12 that supplies priming fluid, a discharging part 14 that discharges the priming fluid, and a supply line LS and a discharge line LD in which the priming fluid flows. The priming fluid used here is not particularly limited if the priming fluid does not affect later treatment and may be, for example, dialysis fluid or may be saline. The configuration of the supplying part 12 is not limited if the priming fluid can be supplied. Therefore, the supplying part 12 may be a dialysis fluid supply device that supplies the dialysis fluid for hemodialysis, or may be a container (e.g., a bottle or a flexible bag) filled with the priming fluid. The supplying part 12 may be a line communicating with a supply source of the priming fluid provided on the outside of the device.

The configuration of the discharging part 14 is not limited if used priming fluid can be discharged. Therefore, the discharging part 14 may be a dialysis fluid discharging device that discharges used dialysis fluid for hemodialysis, or may be a container (e.g., a bottle or a flexible bag) that can store used priming fluid. The discharging part 14 may be a line communicating with a discarding part for the priming fluid provided on the outside of the device.

The supply line LS is connected to the supplying part 12. The discharge line LD is connected to the discharging part 14. A supply connector CS connectable to the venous side connector CV is attached to the distal end (an end portion on an opposite side to the supplying part 12) of the supply line LS. The supply line LS is connectable to the distal end of the venous side line LV. A discharge connector CD connectable to the arterial side connector CA is attached to the distal end (an end portion on an opposite side to the discharging part 14) of the discharge line LD. The discharge line LD is connectable to the distal end of the arterial side line LA. When executing the priming processing, the operator sets a state shown in FIG. 2, that is, a state in which the venous side connector CV, to which the puncture needle 130 is not connected, is connected to the supply connector CS, and the arterial side connector CA, to which the puncture needle 130 is not connected, is connected to the discharge connector CD. When the blood purifying method is executed, the operator sets a state shown in FIG. 1, that is, a state in which, after the connection of the venous side connector CV and the supply connector CS and the connection of the arterial side connector CA and the discharge connector CD are released, the puncture needles 130 are connected to the venous side connector CV and the arterial side connector CA. Note that the venous side connector CV and the supply connector CS and the arterial side connector CA and the discharge connector CD may be connected via other members such as an adapter instead of being directly connected.

A control part 16 (illustration is omitted in FIG. 2 to FIG. 7) that controls driving of various pumps, valves, and electronic devices mounted on the blood purification device 10 is provided in the blood purification device 10. The control part 16 controls the driving of the various electronic devices according to an instruction from an operator. The control part 16 includes, for example, a CPU that performs various arithmetic operations and a memory that stores various kinds of information. The control part 16 may be a single device or may be configured by a plurality of devices communicable with one another. The blood purification device 10 further includes an input device such as a keyboard that receives an instruction from the operator and output devices such as a display and a speaker for outputting various kinds of information to the operator. The input device and an output device are connected to the control part 16 via a bus or the like. The control part 16 executes various kinds of processing according to various instructions input via the input device, and provides various kinds of information to the operator via a output device according to necessity.

A flow of priming processing in such a blood purification device 10 will be explained. When executing the priming processing, as shown in FIG. 2, the operator connects the venous side connector CV to the supply connector CS and connects the arterial side connector CA to the discharge connector CD. In other words, the operator sets a state in which the venous side line LV and the supplying part 12 are connected, and the arterial side line LA and the discharging part 14 are connected. Note that in order to urge the operator to execute such connection, the control part 16 may display, on the display, information indicating connection destinations of the venous side connector CV and the arterial side connector CA. Such display of the information concerning the connection destinations may be performed, for example, when an instruction for priming is received from the operator. When the blood circuit 100 and the blood purifier 110 are replaced, the priming processing is necessary. Therefore, the control part 16 may monitor presence or absence of replacement of the blood circuit 100 and the blood purifier 110 and, when the replacement of the blood circuit 100 and the blood purifier 110 is detected, display information indicating connection destinations on the display or the like. In any case, in a state in which the connectors are appropriately connected by the operator, when receiving an instruction for priming execution from the operator, the control part 16 reversely drives the blood pump PB. Since the blood pump PB is reversely driven, priming fluid supplied from the supplying part 12 flows in the order of the supply line LS, the venous side line LV, the blood purifier 110, the arterial side line LA, and the discharge line LD. Finally, the priming fluid flowing to the discharge line LD reaches the discharging part 14 and is discharged. Note that thick line arrows in FIG. 2 indicate the flow of the priming fluid in the priming processing.

By reversely driving the blood pump PB in this way, the priming fluid flows to the insides of the blood purifier 110 and the blood circuit 100. Air in the blood purifier 110 and the blood circuit 100 is eliminated. Incidentally, according to this embodiment, the priming fluid flows along the axial direction of the blood purifier 110. In other words, in this embodiment, "back filtration" in which the priming fluid flows from the outer side toward the inner side of the purifying member incorporated in the blood purifier 110 does not occur. By feeding the priming fluid without back-filtering the priming fluid, air locks in which the air is held up on the inside of the blood purifier 110 and the like can be effectively prevented.

That is, among the priming methods in the past, the back filtering for feeding the priming fluid from the outer side to the inner side of the purifying member of the blood purifier 110 is often performed. When the back filtration is performed, the priming fluid in a concentrated state flows to a part to which fluid easily flows in the purifying member. Air locks in which air remains in a part to which the fluid flows less easily are likely to occurs. In a back filtration system, it is necessary to feed a large amount of the priming fluid in order to prevent such an air lock. Therefore, significant cost and time are wasted.

On the other hand, in this embodiment, since the priming fluid is fed along the axial direction of the purifying member, the priming fluid easily spreads uniformly over the entire purifying member. As a result, the air lock can be eliminated even with a relatively small amount of the priming fluid. It is possible to reduce cost and time required for the priming processing.

In this embodiment, the priming processing can be performed by only connecting the distal ends of the arterial side line LA and the venous side line LV to the supply line LS and the discharge line LD. In other words, according to this embodiment, it is unnecessary to provide, on the blood circuit 100 side, a branch line and a connector dedicated to the priming processing and that are not necessary for treatment. Consequently, it is possible to reduce work load on the operator.

That is, in the priming method in the past, a branch line dedicated to priming and that is not necessary for treatment is often provided in the blood circuit 100. The branch line that is not necessary for the treatment is often connected to a line provided in the blood purification device 10. The blood circuit 100 is a disposable member discarded and replaced each time of use. Therefore, the operator needs to set the blood circuit 100 in the blood purification device 10 for each time of use. When the branch line that is not necessary for the treatment is present in such a blood circuit 100, confusion of the operator is easily caused. Setting work of the blood circuit 100 is complicated and imposes a load on the operator. When a blood purifying method is executed, such a branch line that is not necessary for the treatment easily hinders the treatment (the blood purifying method).

On the other hand, in this embodiment, as explained above, it is unnecessary to provide a branch line that is dedicated to priming and is not necessary for treatment in the blood circuit 100. Therefore, it is possible to prevent confusion of the operator and effectively prevent misconnection and the like of the blood circuit 100. Since the configuration of the blood circuit 100 can be simplified, it is possible to greatly reduce labor and time for setting the blood circuit 100. Further, since a line not used for the blood purifying method is absent in the blood circuit 100, treatment is not hindered.

Figure 3:
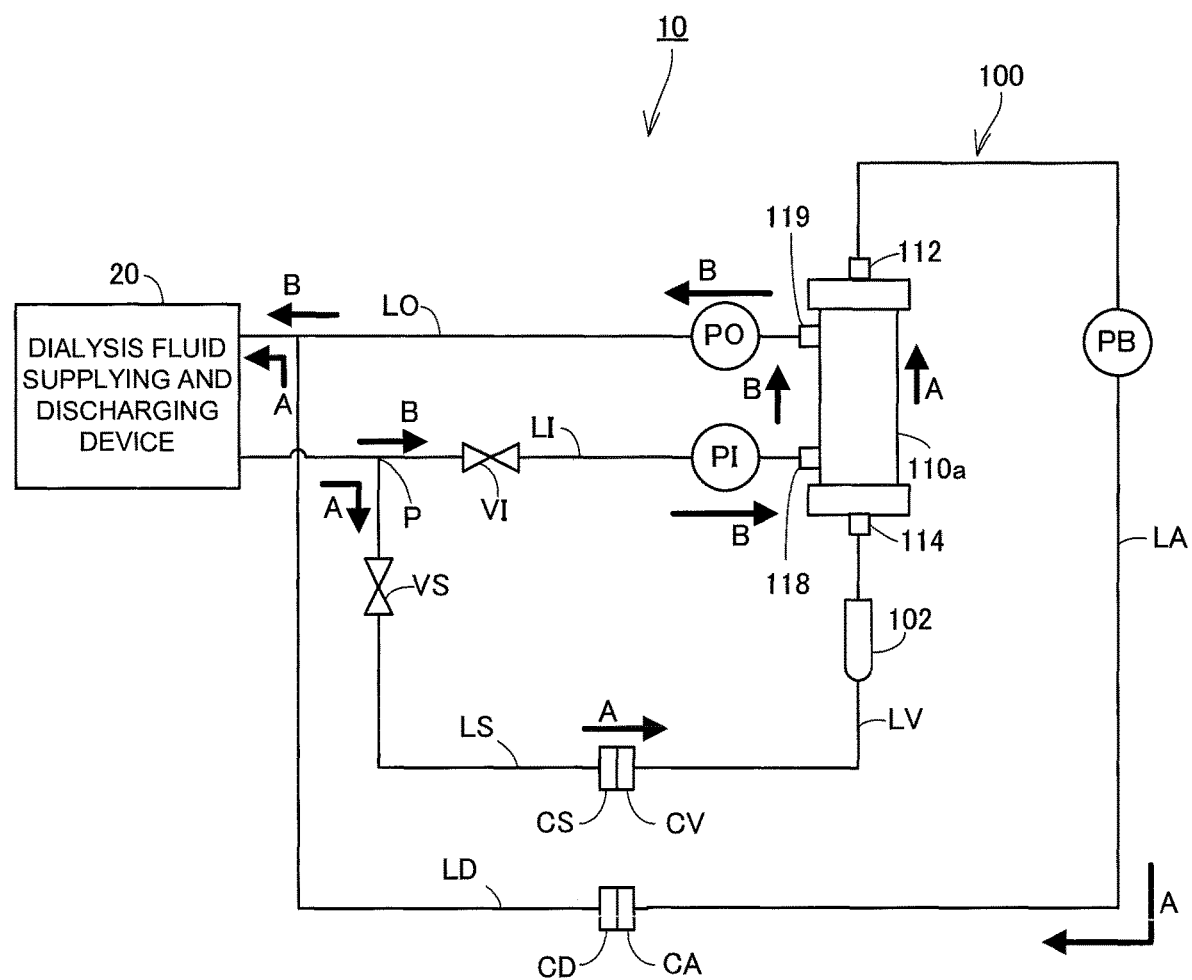
FIG. 3 is a diagram showing the configuration of a blood purification device in a second embodiment of the present invention.

More specific embodiments will be explained with reference to FIG. 3 to FIG. 7. FIG. 3 is a diagram showing the configuration of the blood purification device 10 in a second embodiment. This blood purification device 10 has a configuration particularly suitable in executing hemodialysis. In this case, as the blood purifier 110, a dialyzer 110a, on the inside of which a hollow fiber membrane is provided, is used. The blood inlet 112 and the blood outlet 114 are provided at both ends of the dialyzer 110a in the axial direction. A lead-in port 118, to which dialysis fluid is supplied, and a lead-out port 119, from which the dialysis fluid is discharged, are provided on the circumferential surface of the dialyzer 110a.

In the blood purification device 10, a dialysis fluid supplying and discharging device 20 that supplies and discharges the dialysis fluid is provided. During dialysis treatment, the dialysis fluid is continuously supplied from the dialysis fluid supplying and discharging device 20 to the dialyzer 110a. The dialysis fluid that has passed through the dialyzer 110a is returned to the dialysis fluid supplying and discharging device 20 and discarded. In this embodiment, the dialysis fluid is used as the priming fluid. Therefore, the dialysis fluid supplying and discharging device 20 also functions as a supplying part and a discharging part of the priming fluid.

A lead-in line LI, in which the dialysis fluid supplied from the dialysis fluid supplying and discharging device 20 flows, and a lead-out line LO, in which the dialysis fluid discharged from the dialyzer 110a flows, are connected to the dialysis fluid supplying and discharging device 20. The lead-in line LI connects the dialysis fluid supplying and discharging device 20 and the lead-in port 118. The lead-out line LO connects the dialysis fluid supplying and discharging device 20 and the lead-out port 119. A lead-in pump PI that delivers the dialysis fluid to the dialyzer 110a is provided midway in the lead-in line LI. A lead-out pump PO that delivers the dialysis fluid from the dialyzer 110a to the dialysis fluid supplying and discharging device 20 is provided midway in the lead-out line LO. The configurations of the lead-in pump PI and the lead-out pump PO are not limited if the lead-in pump PI and the lead-out pump PO can respectively deliver the dialysis fluid. Therefore, the lead-in pump PI and the lead-out pump PO may be pumps that can be driven independently from each other, for example, a tube pump. or may be duplex pumps driven in association with each other.

The lead-out line LO branches halfway and configures the discharge line LD. As explained in the first embodiment, the discharge line LD is the line connected to the dialysis fluid supplying and discharging device 20 (the discharging part) and connectable to the distal end of the arterial side line LA. The discharge connector CD connectable to the arterial side connector CA is provided at the distal end of the discharge line LD.

The lead-in line LI branches halfway and configures the supply line LS. As explained in the first embodiment, the supply line LS is the line connected to the dialysis fluid supplying and discharging device 20 (the supplying part) and connectable to the distal end of the venous side line LV. The supply connector CS connectable to the venous side connector CV is provided at the distal end of the supply line LS.

A lead-in valve VI that controls passage of the dialysis fluid is provided further on the dialyzer 110a side than a branch point P in the lead-in line LI. A supply valve VS that allows and prohibits passage of the dialysis fluid is provided further toward the blood circuit 100 side than the branch point P in the supply line LS. The lead-in valve VI and the supply valve VS function as a switching mechanism that switches a supply destination of the dialysis fluid supplied from the dialysis fluid supplying and discharging device 20 to the dialyzer 110a or the supply line LS. When the lead-in valve VI is set in an open state and the supply valve VS is set in a closed state, the dialysis fluid supplied from the dialysis fluid supplying and discharging device 20 is supplied to the dialyzer 110a. On the other hand, when the lead-in valve VI is set to a closed state and the supply valve VS is set to an open state, the dialysis fluid supplied from the dialysis fluid supplying and discharging device 20 is supplied to the supply line LS. Note that the lead-in valve VI and the supply valve VS may be omitted or changed if the supply destination of the dialysis fluid can be switched. For example, a three-way valve may be provided in the branch point P instead of the lead-in valve VI and the supply valve VS. A squeezing-type tube pump can close a tube when driving is stopped. Therefore, the squeezing-type tube pump may be adopted as the lead-in pump PI and the lead-in pump PI may function as a lead-in valve. Further, the blood purification device 10 also includes a control part (not shown in the figure) that controls driving of the pumps PB, PO, and PI and the valves VI and VS.

A flow in priming the blood purifier 110 and the blood circuit 100 in the blood purification device 10 having the configuration explained above will be explained. In this embodiment, when priming is executed, as shown in FIG. 3, the supply line LS is connected to the distal end of the venous side line LV and the discharge line LD is connected to the distal end of the arterial side line LA in advance. If necessary, in order to urge this connection, the control part causes the display or the like to display information indicating connection destinations of the venous side line LV and the arterial side line LA. When receiving an instruction for priming execution in an appropriately connected state, the control part executes, as the priming processing, in order, first priming processing for feeding the dialysis fluid (the priming fluid) in a flow along arrows A, and second priming processing for feeding the dialysis fluid in a flow along arrows B.

When executing the first priming processing, the control part closes the lead-in valve VI, opens the supply valve VS, and switches a supply destination of dialysis fluid supplied from the dialysis fluid supplying and discharging device 20 to the supply line LS. In that state, the control part reversely drives the blood pump PB. As a result of the reverse driving of the blood pump PB, the dialysis fluid supplied from the dialysis fluid supplying and discharging device 20 flows in order to the supply line LS, the venous side line LV, the dialyzer 110a, the arterial side line LA, and the discharge line LD. Finally, the dialysis fluid that has passed through the discharge line LD is returned to the dialysis fluid supplying and discharging device 20 and discarded.

As is evident from the above explanation, in the first priming processing, as in the first embodiment, the dialysis fluid (the priming fluid) flows along the axial direction of the dialyzer 110a. The dialysis fluid is not back-filtered. Therefore, as in the first embodiment, it is possible to prevent the dialysis fluid from flowing to only a portion of the dialyzer 110a, and effectively prevent an air lock.

If the first priming processing is performed for a fixed time, subsequently, the control part executes second priming processing. When executing the second priming processing, the control part opens the lead-in valve VI, closes the supply valve VS, and switches the supply destination of the dialysis fluid supplied from the dialysis fluid supplying and discharging device 20 to the dialyzer 110a. In that state, the control part normally drives the lead-in pump PI and the lead-out pump PO. By normally driving the lead-in pump PI and the lead-out pump PO, the dialysis fluid supplied from the dialysis fluid supplying and discharging device 20 flows in order to the lead-in line LI, the dialyzer 110a, and the lead-out line LO. Note that a part of the dialysis fluid flowing into the dialyzer 110a flows to the arterial side line LA and the venous side line LV as well via the blood inlet 112 and the blood outlet 114. However, the arterial side line LA is closed by the blood pump PB that has been stopped. The supply line LS connected to the venous side line LV is closed by the supply valve VS. Therefore, most of the dialysis fluid flowing into the dialyzer 110a flows from the lead-out port 119 to the lead-out line LO and thereafter returns to the dialysis fluid supplying and discharging device 20, and is discarded.

By performing the second priming processing, the dialysis fluid can be fed to a gap between a housing of the dialyzer 110a and the hollow fiber membrane. The air in the dialyzer 110a can be more reliably eliminated. That is, usually, the dialyzer 110a is configured by disposing the hollow fiber membrane on the inside of a cylindrical housing. However, a very small gap is present between the inner circumferential surface of the housing and the outer circumferential surface of the hollow fiber membrane. When the dialysis fluid is fed along the axial direction of the dialyzer 110a according to the first priming processing, since the dialysis fluid flows less easily out to the outside of the hollow fiber membrane, the air sometimes remains in the gap. On the other hand, by supplying the dialysis fluid from the circumferential surface (the lead-in port 118) of the dialyzer 110a, the dialysis fluid flows easily to the gap as well. The remaining air can be more reliably eliminated.

As is evident from the above explanation, in this embodiment, as in the first embodiment, the dialysis fluid (the priming fluid) is not back-filtered during the priming. Therefore, the remaining air in the dialyzer 110a can be more reliably reduced. Further, in this embodiment, the second priming processing for feeding the dialysis fluid (the priming fluid) from the circumferential surface of the dialyzer 110a is also performed. Therefore, the dialysis fluid can be reliably fed to the periphery of the hollow fiber membrane. The remaining air of the dialyzer 110a can be further reduced.

As is evident from FIG. 3, in this embodiment, the blood circuit 100 does not include a branch line dedicated to priming and that is not necessary for treatment. Therefore, the blood circuit 100 can be simplified. It is possible to reduce labor and time in setting the blood circuit 100 in the blood purification device 10.

Figure 4:
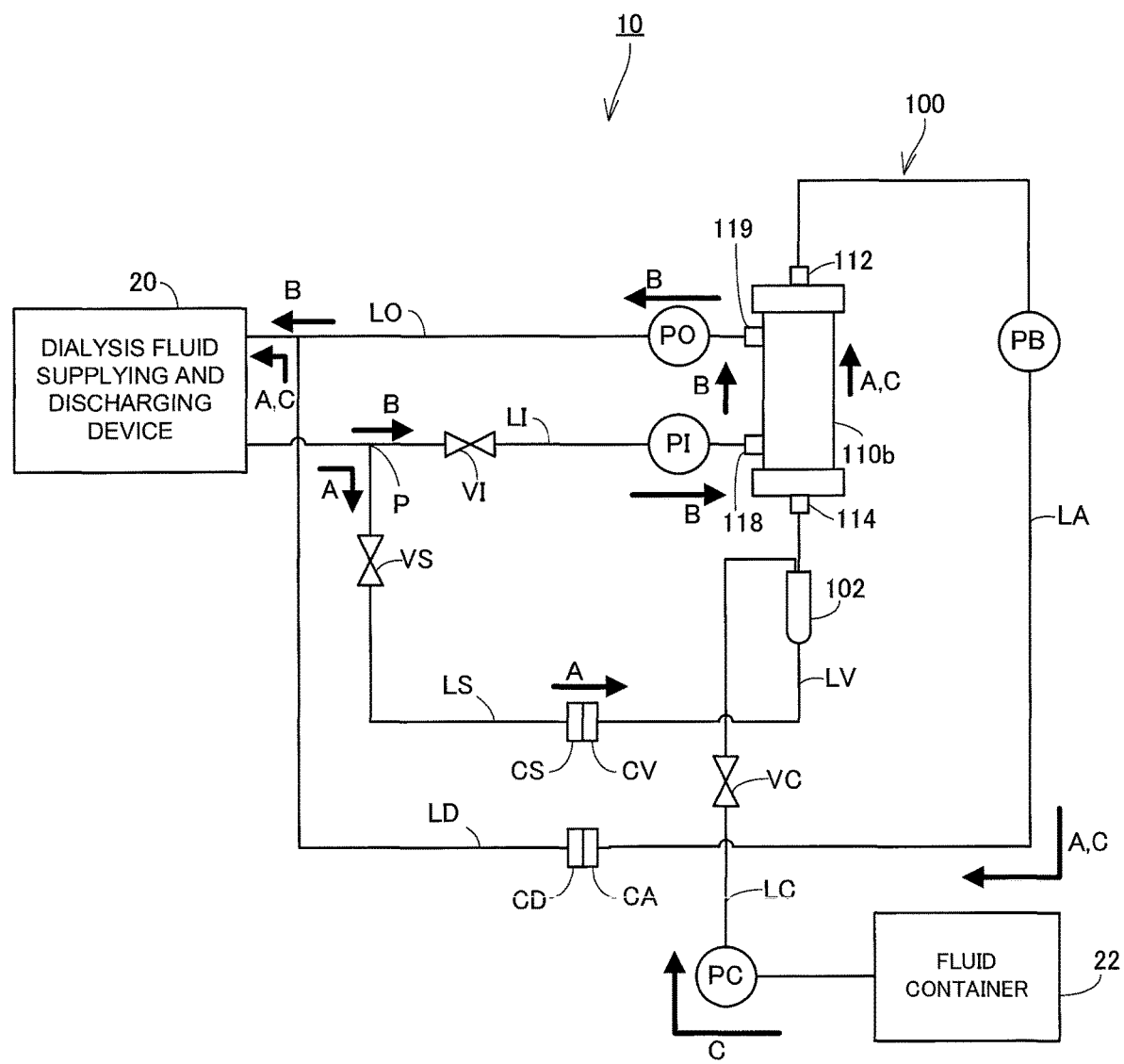
FIG. 4 is a diagram showing the configuration of a blood purification device in a third embodiment of the present invention.

A third embodiment will be explained. FIG. 4 is a diagram showing the configuration of the blood purification device 10 in the third embodiment. This blood purification device 10 has a configuration particularly suitable to executing diafiltration. In this case, as the blood purifier 110, a hemodialysis filter (a hemodiafilter) 110b, on the inside of which a hollow fiber membrane is provided, is used. In the diafiltration, blood is purified by the hemodialysis filter (the hemodiafilter) 110b and replenishment fluid is replenished in the blood to supplement components lost by blood purification. Therefore, a replenishment fluid line LC in which the replenishment fluid flows is provided in the blood circuit 100. The replenishment fluid line LC is a replenishment fluid line connected to one of the arterial side line LA and the venous side line LV. In FIG. 4, a configuration is shown in which the replenishment fluid line LC is connected to the venous side line LV via the air trap chamber 102. The fluid container 22 filled with the replenishment fluid or the priming fluid is connected to the other end of the replenishment fluid line LC. The fluid container 22 is not particularly limited if the fluid container 22 can store fluid. For example, a bottle, a flexible bag, and the like can be used. However, in general, the replenishment fluid is often filled into the flexible bag and treated. Therefore, this fluid container is generally the flexible bag.

In the blood purification device 10, a replenishment fluid pump PC for delivering the replenishment fluid and a replenishment fluid valve VC for opening and closing the replenishment fluid line LC are provided. The blood purification device 10 in this embodiment has substantially the same configuration as the configuration of the blood purification device 10 in the second embodiment (see FIG. 3) except that the blood purification device 10 in this embodiment includes the replenishment fluid pump PC and the replenishment fluid valve VC. Note that if the replenishment fluid pump PC stops and functions as a valve for closing the replenishment fluid line LC, the replenishment fluid valve VC may be omitted. Further, the blood purification device 10 also includes a control part (not shown in the figure) that controls driving of the pumps PB, PO, PI, and PC, and the valves VI, VS, and VC.

A flow of priming performed in the blood purification device 10 in this embodiment will be explained. When the priming processing is performed, the supply line LS is connected to the distal end of the venous side line LV and the discharge line LD is connected to the distal end of the arterial side line LA in advance. If necessary, in order to urge this connection, the control part causes the display or the like to display information indicating connection destinations of the venous side line LV and the arterial side line LA. When receiving an instruction for priming execution in an appropriately connected state, first, the control part performs, as the priming processing, third priming processing for feeding the dialysis fluid in a flow along arrows C. Thereafter, the control part executes, in order, first priming processing for feeding the dialysis fluid (the priming fluid) in a flow along arrows A and second priming processing for feeding the dialysis fluid in a flow along arrows B.

In the third priming processing, the control part closes the supply valve VS and the lead-in valve VI, opens the replenishment fluid valve VC, normally drives the replenishment fluid pump PC, and reversely drives the blood pump PB. At this time, the replenishment fluid or saline functioning as the priming fluid is filled into the fluid container 22. When the replenishment fluid valve VC is normally driven, the priming fluid (the replenishment fluid or the saline) filled into the fluid container 22 flows in the order of the replenishment fluid line LC, the venous side line LV, the hemodialysis filter 110b, the arterial side line LA, and the discharge line LD, and is finally discarded in the dialysis fluid supplying and discharging device 20. Consequently, the replenishment fluid line LC is filled with the priming fluid. The air remaining in the replenishment fluid line LC is eliminated. The first priming processing and the second priming processing performed after the third priming processing are the same as those in the second embodiment. That is, in the first priming processing, the control part reversely drives the blood pump PB in a state in which the lead-in valve VI is closed and the supply valve VS is opened. In the second priming processing, the control part normally drives the lead-in pump PI and the lead-out pump PO in a state in which the supply valve VS is closed and the lead-in valve VI is opened. In the first and second priming processing, the replenishment fluid valve VC is closed to prevent the dialysis fluid (the priming fluid) from flowing back to the fluid container 22 side.

As is evident from the above explanation, in this embodiment, as in the second embodiment, the dialysis fluid (the priming fluid) is not back-filtered during the priming. Therefore, it is possible to more reliably reduce the remaining air in the hemodialysis filter 110b. The second priming processing for feeding the dialysis fluid (the priming fluid) from the circumferential surface of the hemodialysis filter 110b is also performed. Therefore, it is possible to reliably feed the dialysis fluid to the periphery of the hollow fiber membrane as well. It is possible to further reduce the remaining air in the hemodialysis filter 110b. In this embodiment, the third priming processing for feeding the priming fluid to the replenishment fluid line LC is also performed. Therefore, it is possible to eliminate the air in the replenishment fluid line LC as well.

As is evident from FIG. 4, in this embodiment as well, the blood circuit 100 does not include a branch line dedicated to priming and that is not necessary for treatment. Therefore, the blood circuit 100 can be simplified. It is possible to reduce labor and time in setting the blood circuit 100 in the blood purification device 10.

Figure 5:
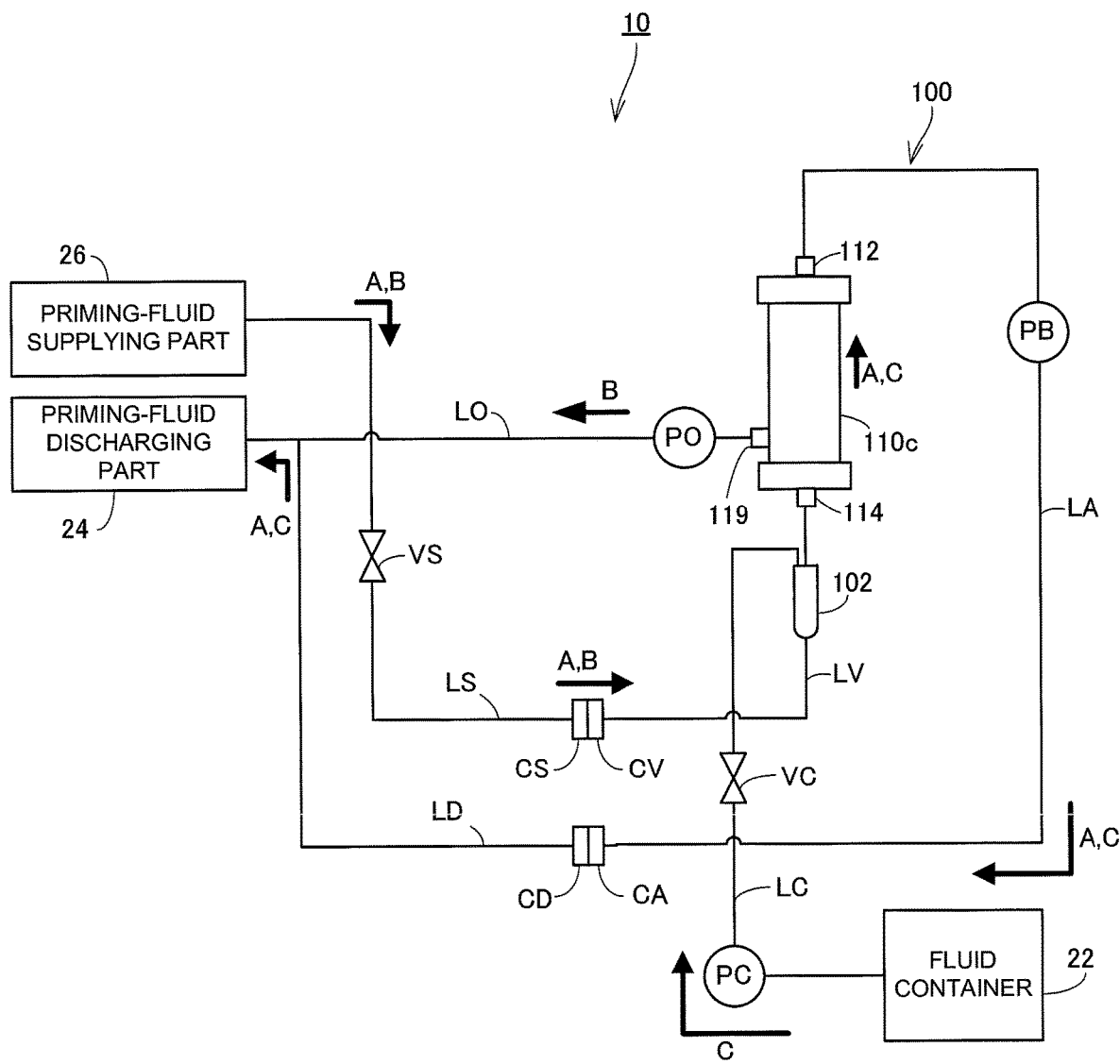
FIG. 5 is a diagram showing the configuration of a blood purification device in a fourth embodiment of the present invention.

A fourth embodiment will be explained with reference to FIG. 5. FIG. 5 is a diagram showing the configuration of the blood purification device 10 in the fourth embodiment. This blood purification device 10 has a configuration particularly suitable to executing hemofiltration. In this case, as the blood purifier 110, a blood filter 110c (a hemofilter), on the inside of which a hollow fiber membrane is provided, is used.

In the hemofiltration, blood is filtrated by the blood filter 110c (the hemofilter) and replenishment fluid is replenished in the blood to supplement components lost in the hemofiltration. On the other hand, in the hemofiltration, supply and discharge of dialysis fluid are not performed. Only discharge of filtrate discharged by the blood filter 110c (the hemofilter) is performed.

Therefore, the blood purification device 10 in this embodiment includes a priming-fluid discharging part 24 that processes filtrate and the lead-out line LO that connects the priming-fluid discharging part 24 and the blood filter 110c. A priming-fluid supplying part 26 that stores the priming fluid is also provided in the blood purification device 10. The priming-fluid supplying part 26 is, for example, a bottle or a flexible bag and functions as a supplying part for the priming fluid. Note that a line connected to a supply source of the priming fluid provided on the outside of the device may be used as the supplying part for the priming fluid instead of the priming-fluid supplying part 26. The supply line LS connectable to the distal end of a vein is connected to the priming-fluid supplying part 26. The discharge line LD connectable to the distal end of an artery joins midway in the lead-out line LO. Further, the blood purification device 10 also includes a control part (not shown in the figure) that controls driving of the pumps PB, PO, and PC and the valves VS and VC.

A flow in performing the priming in the blood purification device 10 in this embodiment will be explained. When the priming processing is executed, as in the first to third embodiments, the supply line LS is connected to the distal end of the venous side line LV and the discharge line LD is connected to the distal end of the arterial side line LA in advance. If necessary, in order to urge this connection, the control part causes the display or the like to display information indicating connection destination of the venous side line LV and the arterial side line LA. When receiving an instruction for priming execution in an appropriately connected state, the control part performs, as the priming processing, the third priming processing for feeding the dialysis fluid in a flow along arrows C. Thereafter, the control part executes the first priming processing for feeding the dialysis fluid (the priming fluid) in a flow along arrows A and the second priming processing for feeding the dialysis fluid (the priming fluid) in a flow along arrows B. That is, first, as the third priming processing, the control part normally drives the replenishment fluid pump PC and reversely drives the blood pump PB in a state in which the supply valve VS is closed and the replenishment fluid valve VC is opened. At this time, the replenishment fluid or the saline is filled into the fluid container 22 connected to the replenishment fluid line LC as the priming fluid. Thereafter, as the first priming processing, the control part reversely drives the blood pump PB in a state in which the supply valve VS is opened and the replenishment fluid valve VC is closed. If the first priming processing ends, subsequently, the control part executes the second priming processing. That is, the control part stops the blood pump PB and, on the other hand, normally drives the lead-out pump PO while maintaining the state in which the supply valve VS is opened and the replenishment fluid valve VC is closed.

The first priming processing, the second priming processing, and the third priming processing are performed in this way, whereby the priming fluid flows to the venous side line LV, the arterial side line LA, the lead-out line LO, the replenishment fluid line LC, and the blood filter 110c, and the remaining air is eliminated. In particular, in this embodiment, as in the first to third embodiments, since the back filtration is not performed, air lock of the blood filter 110c can be effectively prevented. In this embodiment, as in the first to third embodiments, the blood circuit 100 does not include a branch line dedicated to priming and that is not necessary for treatment. Therefore, the blood circuit 100 can be simplified. It is possible to reduce labor and time in setting the blood circuit 100 in the blood purification device 10.

Figure 6:
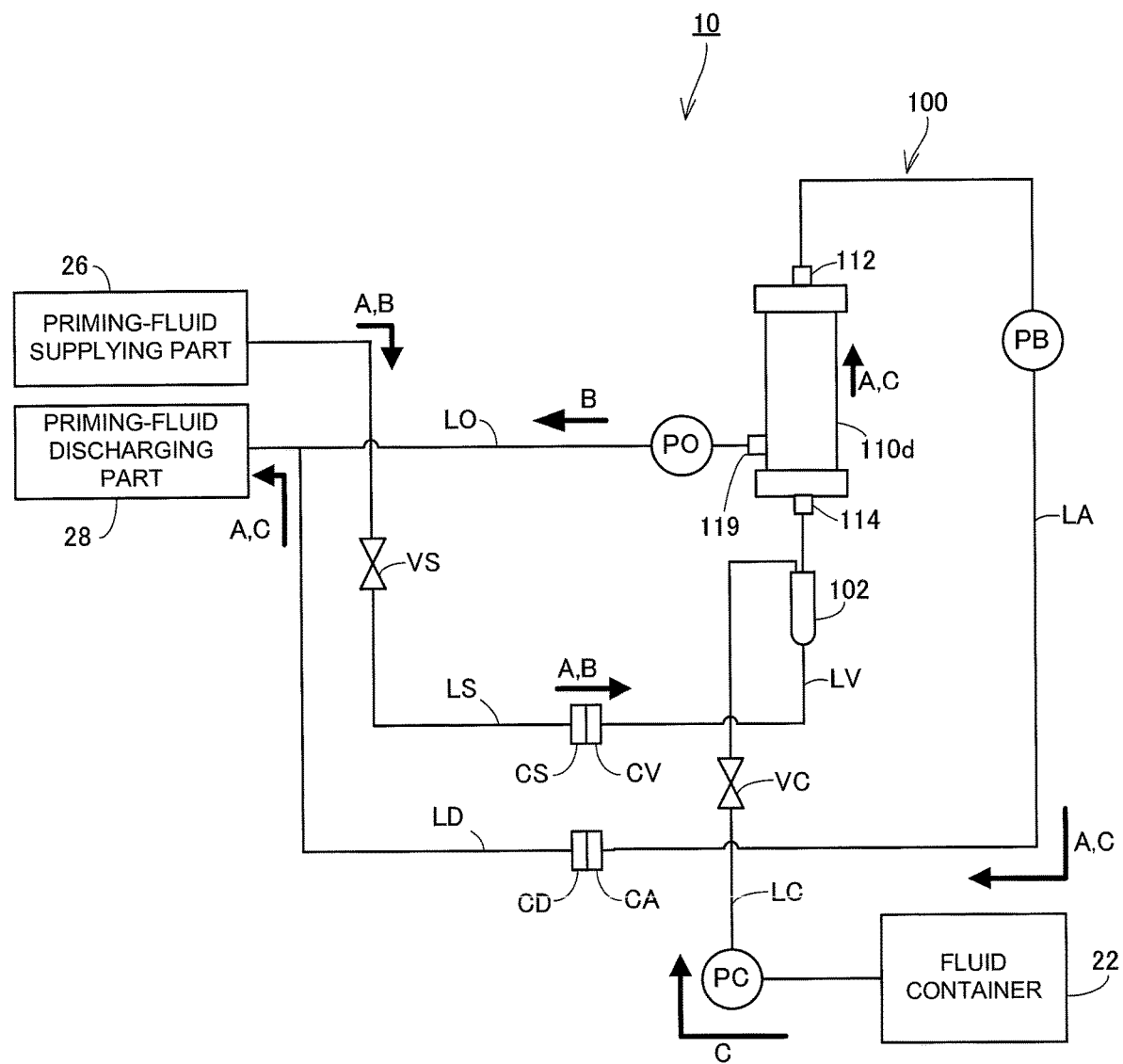
FIG. 6 is a diagram showing the configuration of a blood purification device in a fifth embodiment of the present invention.

A fifth embodiment will be explained with reference to the drawings. FIG. 6 is a diagram showing the configuration of the blood purification device 10 in the fifth embodiment. This blood purification device 10 has a configuration particularly suitable to executing simple plasmapheresis. In this case, a plasma separator 110d, on the inside of which a hollow fiber membrane is provided, is used as the blood purifier 110.

In the simple plasmapheresis, a plasma component is removed from blood by the plasma separator 110d and replenishment fluid (fresh frozen plasma, etc.) is replenished in the blood to supplement the removed component. The plasma component separated by the plasma separator 110d is collected and discarded. Therefore, the blood purification device 10 in this embodiment includes a priming-fluid discharging part 28 that processes a plasma component and the lead-out line LO that connects the priming-fluid discharging part 28 and the plasma separator 110d. The priming-fluid discharging part 28 also functions as a discharging part that discharges used priming fluid. The priming-fluid supplying part 26 that stores the priming fluid is also provided in the blood purification device 10. This priming-fluid supplying part 26 is, for example, a bottle or a flexible bag and functions as a supplying part for the priming fluid. Note that a line connected to a supply source of the priming fluid provided on the outside of the device may be used as the supplying part instead of the priming-fluid supplying part 26. The supply line LS connectable to the distal end of a vein is connected to the priming-fluid supplying part 26. The discharge line LD connectable to the distal end of an artery joins midway in the lead-out line LO. Further, the blood purification device 10 also includes a control part (not shown in the figure) that controls driving of the pumps PB, PO, and PC and the valves VS and VC.

A flow of the priming processing in the blood purification device 10 having the configuration explained above is substantially the same as the flow in the fourth embodiment. That is, when the priming processing is executed, the supply line LS is connected to the distal end of the venous side line LV and the discharge line LD is connected to the distal end of the arterial side line LA in advance. If necessary, in order to urge this connection, the control part causes the display or the like to display information indicating connection destinations of the venous side line LV and the arterial side line LA. When receiving an instruction for priming execution in an appropriately connected state, the control part performs, as the priming processing, the third priming processing for feeding the priming fluid in a flow along arrows C. Thereafter, the control part executes the first priming processing for feeding the priming fluid in a flow along arrows A and the second priming processing for feeding the priming fluid in a flow along arrows B. That is, first, as the third priming processing, the control part normally drives the replenishment fluid pump PC and reversely drives the blood pump PB in a state in which the supply valve VS is closed and the replenishment fluid valve VC is opened. At this time, the saline is filled into the fluid container 22 connected to the replenishment fluid line LC as the priming fluid. As the first priming processing, the control part reversely drives the blood pump PB in a state in which the supply valve VS is opened and the replenishment fluid valve VC is closed. If the first priming processing ends, subsequently, the control part executes the second priming processing. That is, the control part stops the blood pump PB and, on the other hand, normally drives the lead-out pump PO while maintaining the state in which the supply valve VS is opened and the replenishment fluid valve VC is closed.

As is evident from the above explanation, in this embodiment, as in the first to fourth embodiments, since the back filtration is not performed, air lock of the blood purifier 110 can be effectively prevented. In this embodiment, as in the first to fourth embodiments, the blood circuit 100 does not include a branch line dedicated to priming and that is not necessary for treatment. Therefore, the blood circuit 100 can be simplified. It is possible to reduce labor and time in setting the blood circuit 100 in the blood purification device 10.

Figure 7:
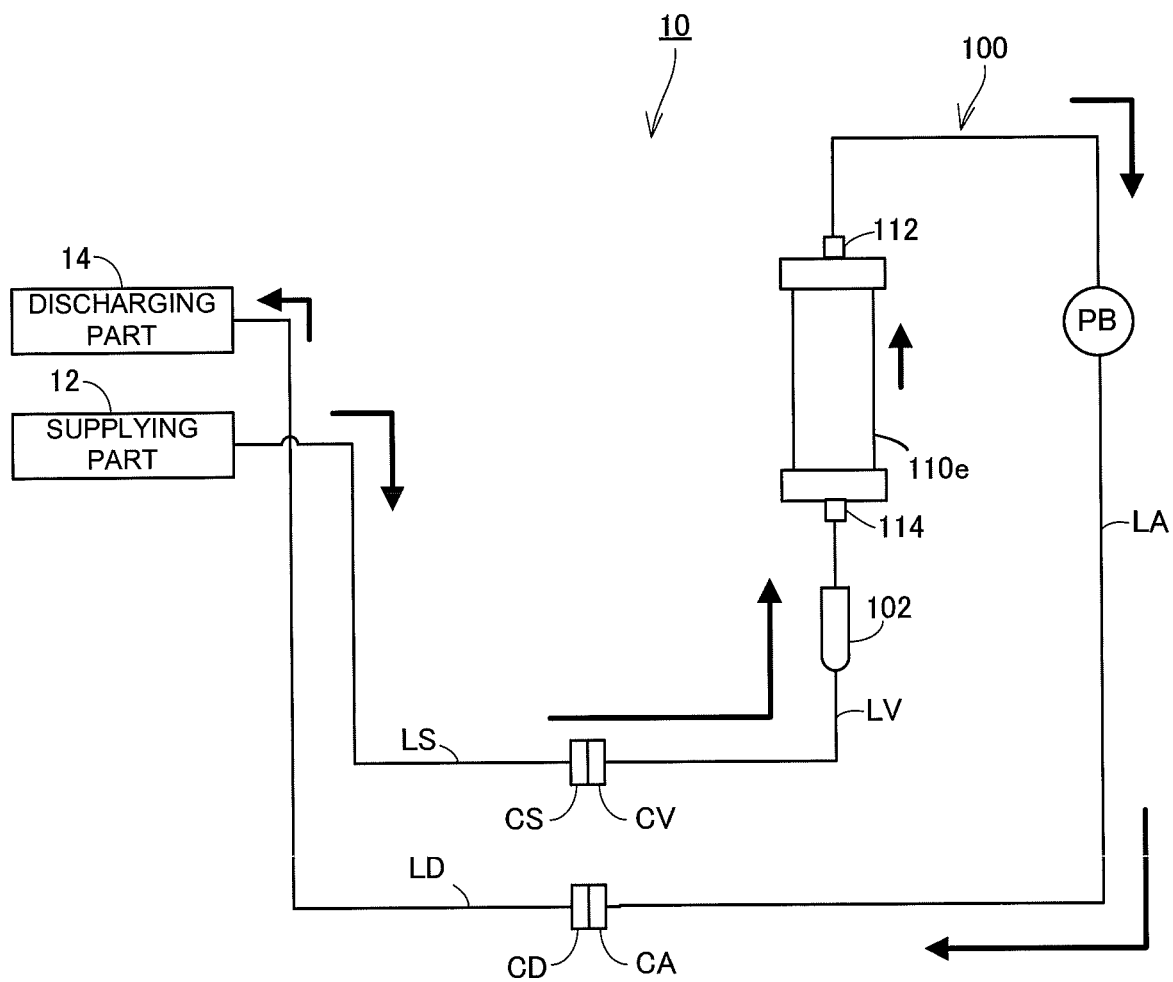
FIG. 7 is a diagram showing the configuration of a blood purification device in a sixth embodiment of the present invention.

A sixth embodiment will be explained with reference to the drawings. FIG. 7 is a diagram showing the configuration of the blood purification device 10 in the sixth embodiment. This blood purification device 10 has a configuration particularly suitable to executing direct blood perfusion. In this case, a blood purification column 110e, on the inside of which an absorbent is provided, is used as the blood purifier 110.

In the direct blood perfusion, an etiology related substance in blood is absorbed by the absorbent and removed. In this case, the blood purification device 10 includes the supplying part 12 of the priming fluid and the discharging part 14 of the priming fluid. Both of the supplying part 12 and the discharging part 14 are containers that can store fluid, or lines connected to a supply source of the priming fluid provided outside the device or a discarding part of the priming fluid. The containers that can store fluid may be, for example, besides containers that keep fixed shapes such as bottles or tanks, a fluid bag or the like formed by a flexible film.

In this case, the supply line LS is connected to the supplying part 12 and the discharge line LD is connected to the discharging part 14. When the priming processing is performed, as in the first embodiment, the supply line LS is connected to the distal end of the venous side line LV and the discharge line LD is connected to the distal end of the arterial side line LA. If necessary, in order to urge this connection, the control part causes the display or the like to display information indicating connection destinations of the venous side line LV and the arterial side line LA. When receiving an instruction for priming execution in an appropriately connected state, the control part reversely drives the blood pump PB in a state in which the supply valve VS is opened and the replenishment fluid valve VC is closed. Consequently, the priming fluid flows in the axial direction of the blood purification column 110e. Air is eliminated from the insides of the blood purification column 110e and the blood circuit 100.

As is evident from the above explanation, in this embodiment, as in the first embodiment, since the back filtration is not performed, air lock of the blood purification column 110e can be effectively prevented. In this embodiment, as in the first to fifth embodiments, the blood circuit 100 does not include a branch line dedicated to priming and that is not necessary for treatment. Therefore, the blood circuit 100 can be simplified. It is possible to reduce labor and time in setting the blood circuit 100 in the blood purification device 10.

Note that the configurations explained above are examples. If the blood purification device 10 includes the supply line LS connected to the supplying part 12 that supplies the priming fluid and connectable to the distal end of the venous side line LV and the discharge line LD connected to the discharging part 14 that discharges the priming fluid after use and connectable to the distal end of the arterial side line LA, the other configuration may be changed as appropriate. The blood purification device 10 explained above can be applied to, for example, a dialysis treatment method, a continuous renal replacement therapy, and apheresis. The configurations shown in FIG. 3 to FIG. 5 are suitable for the dialysis treatment method and the continuous renal replacement therapy. The configurations shown in FIG. 6 and FIG. 7 are suitable for the apheresis.

Figure 8:
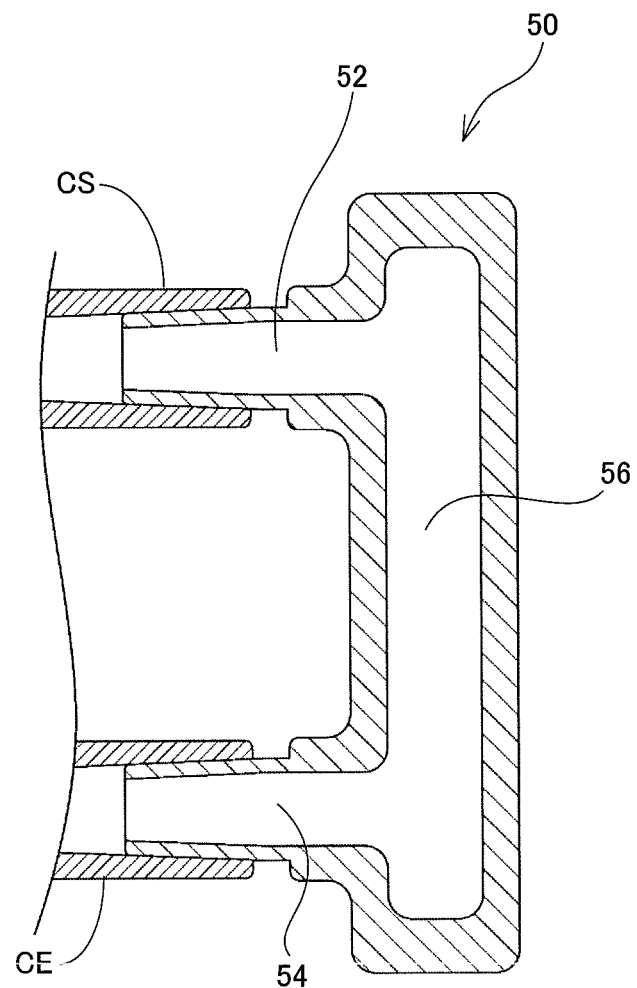
FIG. 8 is a diagram showing an example of a cleaning cap.

Note that when the supply line LS and the discharge line LD are provided in the blood purification device 10, it is desirable that these two lines LD and LS are periodically cleaned. In order to easily perform the cleaning, it is desirable to prepare a cleaning cap 50 that causes the supply connector CS and the discharge connector CD to communicate. FIG. 8 is a diagram showing an example of the cleaning cap 50. The cleaning cap 50 includes a first cylinder part 52 that liquid-tightly communicates with the supply connector CS, a second cylinder part 54 that liquid-tightly communicates with the discharge connector CD, and a communication part 56 that causes the first cylinder part 52 and the second cylinder part 54 to communicate. By attaching the cleaning cap 50 to the supply connector CS and the discharge connector CD, the supply line LS and the discharge line LD communicate via the cleaning cap 50. In this state, if cleaning fluid is supplied from the supplying part 12 of the priming fluid instead of the priming fluid, the cleaning fluid can be continuously fed to the supply line LS and the discharge line LD. Both of the lines LS and LD can be easily cleaned.

Figure 9:
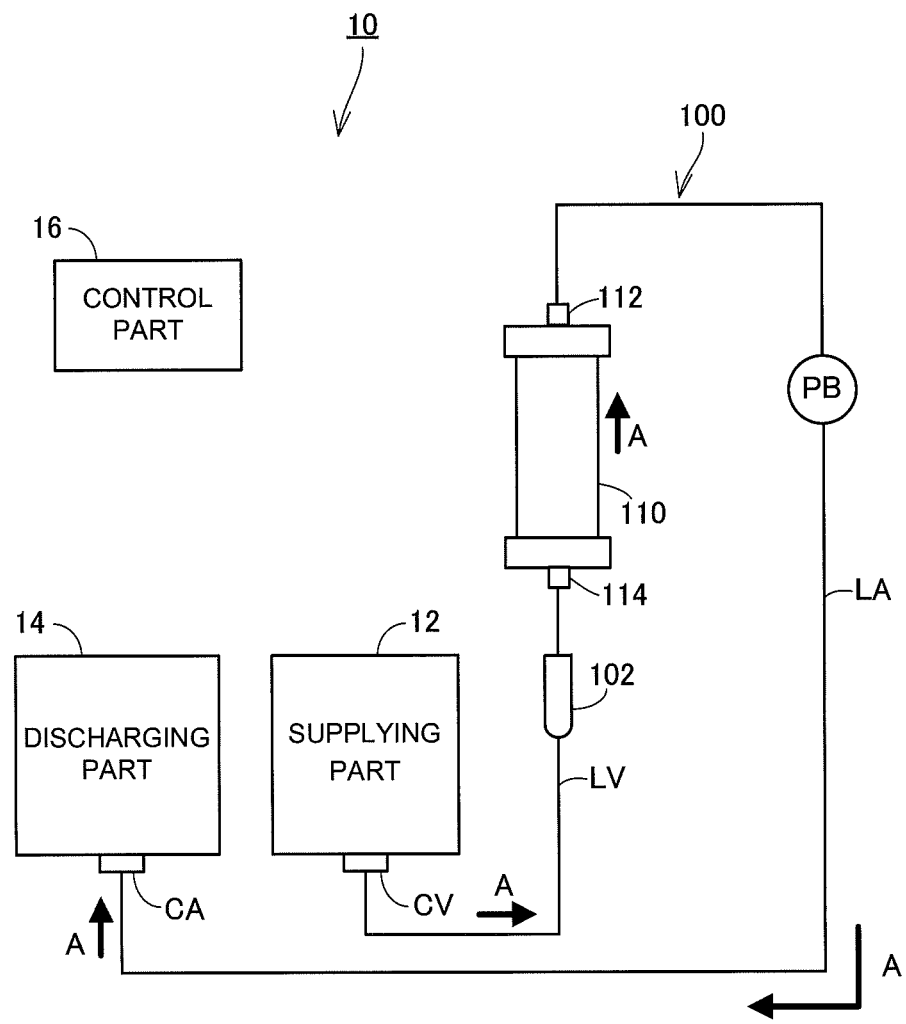
FIG. 9 is a diagram showing the configuration of a blood purification device in a seventh embodiment of the present invention.

A basic embodiment of another present invention is explained with reference to FIG. 9. FIG. 9 is a diagram showing the configuration of the blood purification device 10 in the basic embodiment (a seventh embodiment) of the other present invention. In FIG. 9, only basic components are illustrated. However, other components may be added to the blood purification device 10 as appropriate according to a type of a blood purifying method to be executed. Examples of the blood purifying method executed by the blood purification device 10 include hemodialysis, hemofiltration, diafiltration, direct blood perfusion, and simple plasmapheresis. Examples of the components that can be added to the blood purification device 10 shown in FIG. 9 include a dialysis fluid supplying and discharging device that supplies and discharges dialysis fluid, a pump for delivering the dialysis fluid, and a line and a pump for supplying replenishment fluid for supplementing components removed by blood purification.

The blood purification device 10 shown in FIG. 9 is used in a state in which a consumable unit is set. The consumable unit includes the blood purifier 110 and the blood circuit 100. The configurations of the blood purifier 110 and the blood circuit 100 are the same as the configurations explained with reference to the drawings of FIG. 1 to FIG. 7. Therefore, detailed explanation of these configurations is omitted here. During priming, in addition to the blood circuit 100 and the blood purifier 110, the supplying part 12 that supplies priming fluid and the discharging part 14 from which the priming fluid after use is discharged are also set in the blood purification device 10. That is, in the blood purification device 10 shown in FIG. 9, the supplying part 12 and the discharging part 14 are provided on the outside of the blood purification device 10.

The supplying part 12 is not particularly limited if the supplying part 12 can store a sufficient amount of the priming fluid. Therefore, as the supplying part 12, for example, a flexible bag (a so-called saline bag) or the like that stores saline can be used. The discharging part 14 is not particularly limited if the discharging part 14 can store a sufficient amount of the priming fluid. Therefore, as the discharging part 14, a flexible bag, a bottle, and the like can be used. When the priming processing is performed, as shown in FIG. 9, the venous side line LV is connected to the supplying part 12 via the venous side connector CV. The arterial side line LA is connected to the discharging part 14 via the arterial side connector CA.

The blood purification device 10 includes the blood pump PB for delivering blood. As shown in FIG. 9, the blood pump PB is provided midway in the arterial side line LA. This blood pump PB is normally driven, whereby the blood is sent to a downstream side (the blood purifier 110 side). As explained in detail below, during the priming processing, the blood pump PB is reversely driven and also plays a role of feeding the priming fluid. The configuration of the blood pump PB is not particularly limited. However, in this embodiment, the blood pump PB is a squeezing-type tube pump. The arterial side line LA formed by a flexible tube is squeezed, whereby the blood pump PB delivers the blood, the priming fluid, and the like.

The blood purification device 10 includes the control part 16 that controls at least driving of the blood pump PB. The control part 16 controls driving of various electronic devices according to an instruction from the operator. The control part 16 includes, for example, a CPU that performs various arithmetic operations and a memory that stores various kinds of information. The control part 16 may be a single device or may be configured by a plurality of devices communicable with one another. The blood purification device 10 further includes an input device such as a keyboard that receives an instruction from the operator and output devices such as a display and a speaker for outputting various kinds of information to the operator. The input device and an output device are connected to the control part 16 via a bus or the like. The control part 16 executes various kinds of processing according to various instructions input via the input device and provides various kinds of information to the operator via a output device according to necessity.

The control part 16 controls driving of the blood pump PB and the like according to an instruction from the operator and causes the blood purification device 10 to execute the blood purifying method. Prior to the execution of the blood purification, the control part 16 also performs first priming processing for filling the insides of the blood purifier 110 and the blood circuit 100 with fluid.

A flow of the priming processing in such a blood purification device 10 will be explained. When executing the priming processing, as shown in FIG. 9, the operator connects the venous side line LV to the supplying part 12 via the venous side connector CV and connects the arterial side line LA to the discharging part 14 via the arterial side connector CA. Note that in order to urge the operator to execute such connection, the control part 16 may display, on the display, information indicating connection destinations of the venous side connector CV and the arterial side connector CA. Such display of the information concerning the connection destinations may be performed, for example, when an instruction for priming is received from the operator. When the blood circuit 100 and the blood purifier 110 are replaced, the priming processing is necessary. Therefore, the control part 16 may monitor presence or absence of replacement of the blood circuit 100 and the blood purifier 110 and, when the replacement of the blood circuit 100 and the blood purifier 110 is detected, display information indicating connection destinations on the display or the like. In any case, in a state in which the connectors are appropriately connected by the operator, when receiving an instruction for priming execution from the operator, the control part 16 reversely drives the blood pump PB and executes the first priming processing for priming the blood circuit 100 and the blood purifier 110. Since the blood pump PB is reversely driven, priming fluid supplied from the supplying part 12 flows in the order of the supplying part 12, the venous side line LV, the blood purifier 110, the arterial side line LA, and the discharging part 14. Note that thick line arrows in FIG. 9 indicate the flow of the priming fluid in the priming processing.

As is evident from the above explanation, in the blood purification device 10 shown in FIG. 9, as in the blood purification devices shown in FIG. 1 to FIG. 7, "back filtration" in which the priming fluid flows from the outer side to the inner side of a purifying member provided in the blood purifier 110 does not occur. As a result, air lock in which the air is held up on the inside of the blood purifier 110 and the like can be effectively prevented.

In the blood purification device 10 shown in FIG. 9 as well, it is unnecessary to provide, on the blood circuit 100 side, a branch line and a connector dedicated to the priming processing and that are not necessary for treatment. Consequently, it is possible to reduce a work load on the operator.

Figure 10:
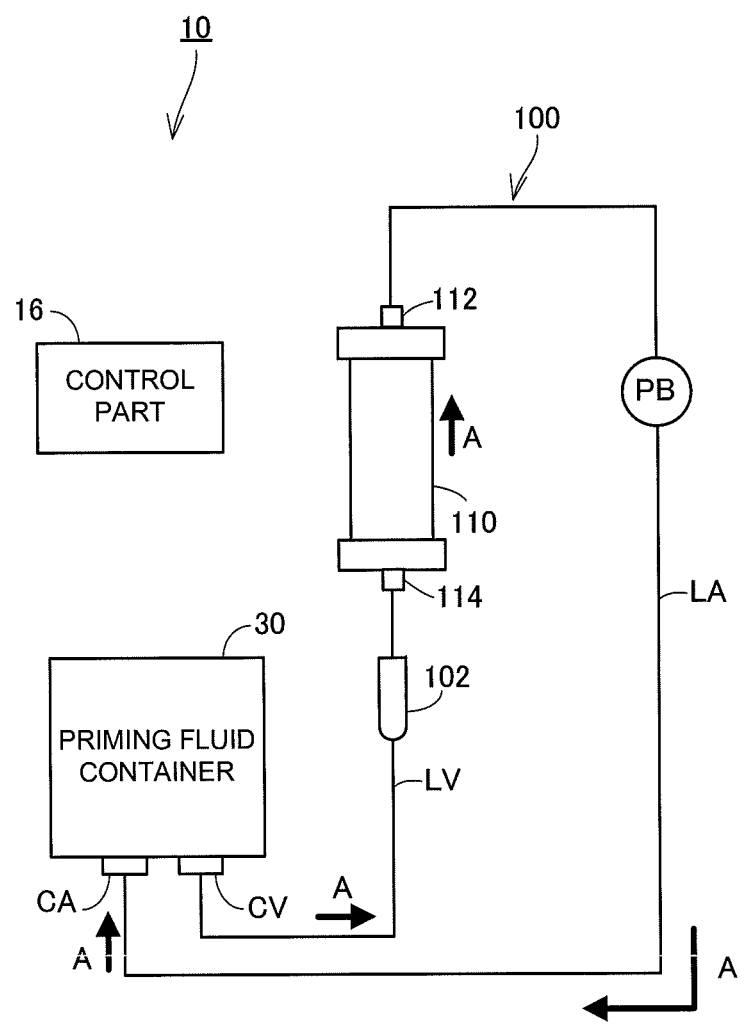
FIG. 10 is a diagram showing a modification of the blood purification device shown in FIG. 9.

Note that in FIG. 9, the supplying part 12 and the discharging part 14 are separated. However, the supplying part 12 and the discharging part 14 may be the same member. That is, as shown in FIG. 10, a priming fluid container 30 functioning as the supplying part 12 and functioning as the discharging part 14 may be prepared. In this case, when performing the priming processing, the operator connects both of the venous side line LV and the arterial side line LA to the priming fluid container 30. By adopting such a configuration, it is possible to reduce the number of containers that store the priming fluid and more easily execute the priming processing.

Figure 11:
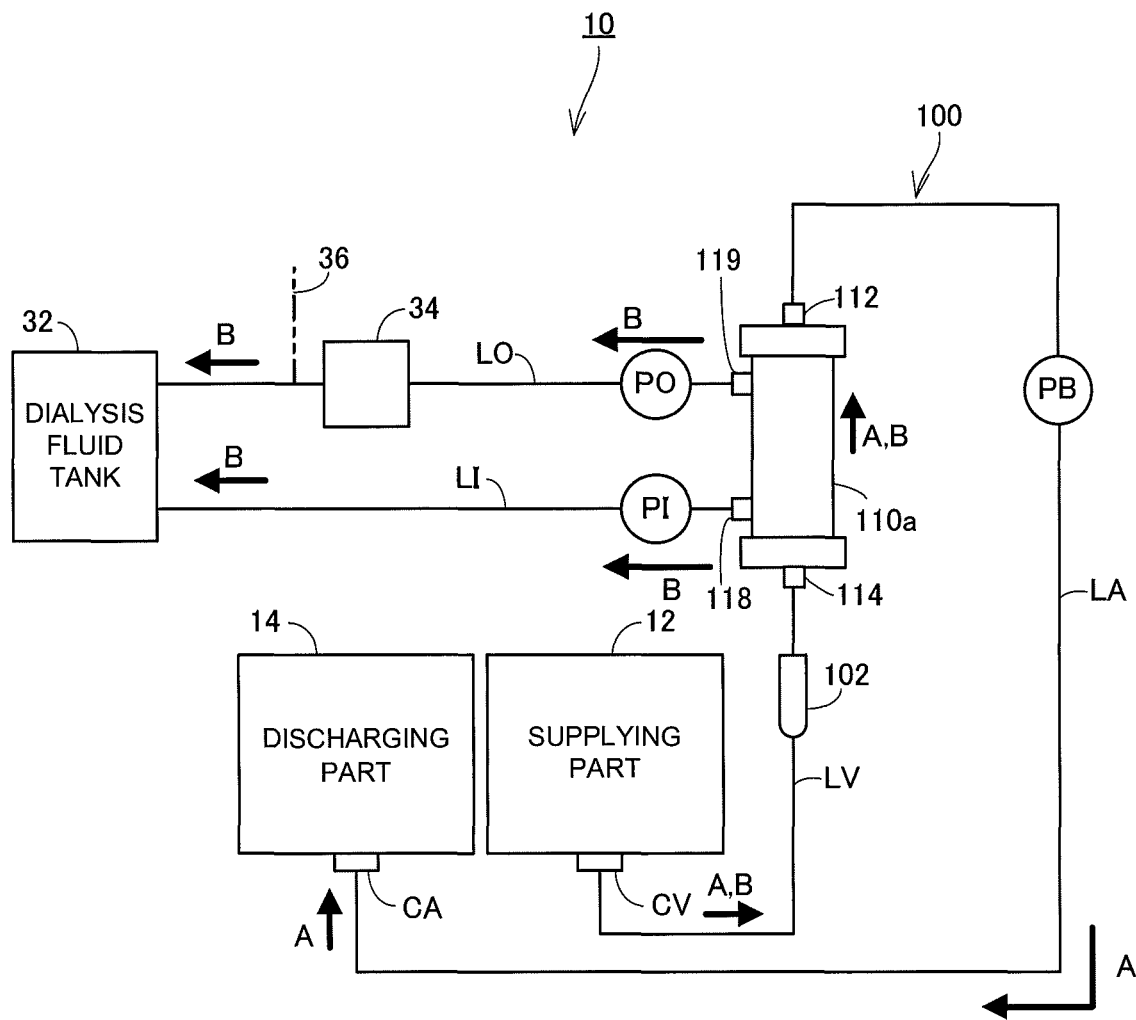
FIG. 11 is a diagram showing the configuration of a blood purification device in an eighth embodiment of the present invention.
Figure 12:
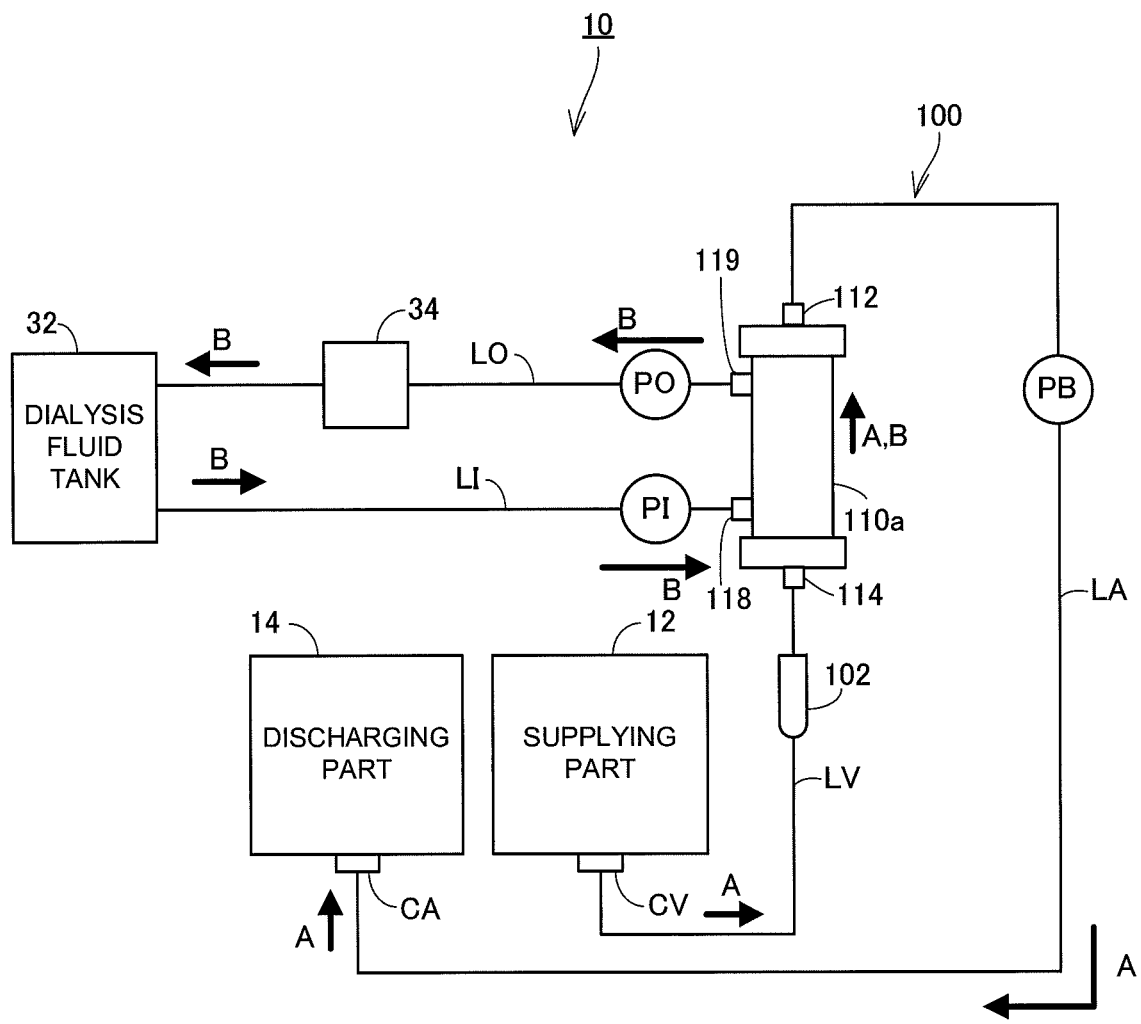
FIG. 12 is a diagram showing the configuration of a modification of the blood purification device shown in FIG. 10.

More specific embodiments will be explained with reference to FIG. 11 to FIG. 14. FIG. 11 is a diagram showing the configuration of the blood purification device 10 in an eighth embodiment. This blood purification device 10 has a configuration particularly suitable to executing hemodialysis. In this case, the dialyzer 110a, on the inside of which a hollow fiber membrane is provided, is used as the blood purifier 110. The blood inlet 112 and the blood outlet 114 are provided at both ends of the dialyzer 110a in the axial direction. The lead-in port 118, to which dialysis fluid is supplied, and the lead-out port 119, from which the dialysis fluid is discharged, are provided on the circumferential surface of the dialyzer 110a.

The blood purification device 10 further includes the lead-in line LI, the lead-out line LO, the lead-in pump PI, the lead-out pump PO, a dialysis fluid tank 32, and a dialysis fluid reproduction column 34, in addition to the control part (not shown in the figure) and the blood pump PB. The lead-in line LI is a line that connects the dialysis fluid tank 32 and the lead-in port 118. The lead-in pump PI is provided midway in the lead-in line LI. A direction of normal driving of the lead-in pump PI is a direction in which the dialysis fluid in the dialysis fluid tank is delivered to the dialyzer 110a. The lead-out line LO is a line that connects the lead-out port 119 and the dialysis fluid tank 32. The lead-out pump PO is provided midway in the lead-out line LO. A direction of normal driving of the lead-out pump PO is a direction in which the dialysis fluid is delivered from the dialyzer 110a to the dialysis fluid tank 32. The configurations of the lead-in pump PI and the lead-out pump PO are not limited if the lead-in pump PI and the lead-out pump PO can respectively deliver the dialysis fluid. Therefore, the lead-in pump PI and the lead-out pump PO may be pumps that can be driven independently from each other, for example, tube pumps, or may be duplex pumps driven in association with each other.

The dialysis fluid reproduction column 34 is provided between the lead-out pump PO and the dialysis fluid tank 32. The dialysis fluid reproduction column 34 removes unnecessary objects from the dialysis fluid after being used for treatment (discharge fluid) and brings the dialysis fluid after use into a state of being reusable as the dialysis fluid. The dialysis fluid reproduced by the dialysis fluid reproduction column 34 is sent to the dialysis fluid tank 32. Note that according to necessity, a replenishment line 36 for replenishing insufficient components to the dialysis fluid after reproduction may be connected to a downstream side of the dialysis fluid reproduction column 34.

The dialysis fluid tank 32 is a tank that temporarily stores the dialysis fluid. The dialysis fluid tank 32 also functions as a second discharging part from which used priming fluid is discharged in the priming processing.

In the blood purification device 10 having the configuration explained above, a flow in priming the dialyzer 110a and the blood circuit 100 has been explained. In this embodiment, when the priming is executed, as shown in FIG. 11, the venous side line LV is connected to the supplying part 12 and the arterial side line LA is connected to the discharging part 14 in advance. If necessary, in order to urge this connection, the control part causes the display or the like to display information indicating connection destinations of the venous side line LV and the arterial side line LA. When receiving an instruction for priming execution in an appropriately connected state, the control part performs, as the priming processing, in order, first priming processing for feeding the priming fluid in a flow along arrows A and second priming processing for feeding the dialysis fluid in a flow along arrows B.

When executing the first priming processing, the control part reversely drives the blood pump PB in a state in which the lead-in pump PI and the lead-out pump PO are stopped. According to the reverse driving of the blood pump PB, the dialysis fluid supplied from the supplying part 12 flows in order to the venous side line LV, the dialyzer 110a, the arterial side line LA, and the discharging part 14.

In the first priming processing, the priming fluid flows along the axial direction of the dialyzer 110a. The dialysis fluid is not back-filtered. Therefore, it is possible to prevent the dialysis fluid from flowing to only a part of the dialyzer 110a. Air lock can be effectively prevented.

If the first priming processing is performed for a fixed time, subsequently, the control part executes the second priming processing. When executing the second priming processing, the control part stops the blood pump PB, normally drives the lead-out pump PO, and reversely drives the lead-in pump PI. The lead-in pump PI is reversely driven and the lead-out pump PO is normally driven, whereby the dialysis fluid supplied from the supplying part 12 flows in the same direction in both of the lead-in line LI and the lead-out line LO, and is discharged to the dialysis fluid tank 32. By performing the second priming processing, the priming fluid can also be fed to a gap between the housing of the dialyzer 110a and the hollow fiber membrane. Air in the dialyzer 110a can be more reliably eliminated. By performing the second priming processing, the priming fluid can also be fed to the dialysis fluid reproduction column 34 provided midway in the lead-out line LO. Air in the dialysis fluid reproduction column 34 can also be eliminated. By normally driving the lead-out pump PO and reversely driving the lead-in pump, the second priming processing can be appropriately executed in advance even if the dialysis fluid tank 32 is empty.

Note that if a sufficient amount of the priming fluid is stored in the dialysis fluid tank 32 in advance, in the second priming processing, the lead-in pump PI may be normally driven. That is, as indicated by arrows B in FIG. 12, in the second priming processing, the control part may stop the blood pump PB, normally drive the lead-out pump PO, and normally drive the lead-in pump PI. In this case, the priming fluid stored in the dialysis fluid tank 32 circulates to return to the dialysis fluid tank 32 through the lead-in line LI, the dialyzer 110a, and the lead-out line LO. Even in this case, the priming fluid can be fed to the gap between the housing of the blood purifier 110 and the hollow fiber membrane. Air in the dialyzer 110a can be more reliably eliminated. By performing the second priming processing, the priming fluid can also be fed to the dialysis fluid reproduction column 34 provided midway in the lead-out line LO. Air in the dialysis fluid reproduction column 34 can also be eliminated. Further, by circulating the priming fluid, a priming fluid amount necessary for the second priming processing can be reduced.

Figure 13:
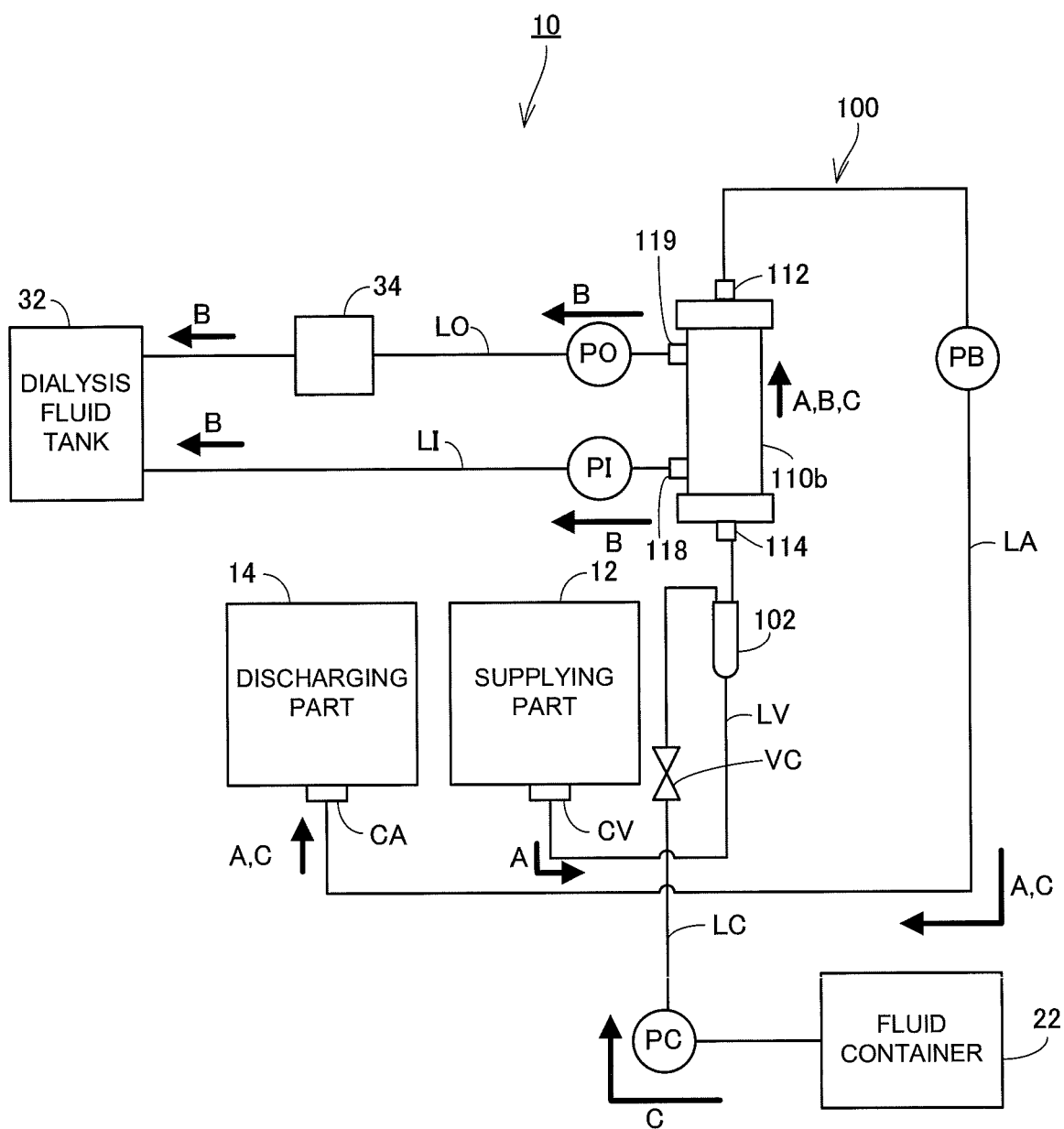
FIG. 13 is a diagram showing the configuration of a blood purification device in a ninth embodiment of the present invention.

A ninth embodiment will be explained. FIG. 13 is a diagram showing the configuration of the blood purification device 10 in the ninth embodiment. This blood purification device 10 has a configuration particularly suitable to executing diafiltration. In this case, as the blood purifier 110, the hemodialysis filter (the hemodiafilter) 110b, on the inside of which the hollow fiber membrane is provided, is used. In the blood circuit 100, the replenishment fluid line LC for replenishing components lost in a process of blood purification (diafiltration) is provided. The fluid container 22 filled with the replenishment fluid or the priming fluid is connected to one end of the replenishment fluid line LC.

In the blood purification device 10, the replenishment fluid pump PC for delivering the replenishment fluid and the replenishment fluid valve VC for opening and closing the replenishment fluid line LC are provided. Note that the replenishment fluid valve VC may be omitted if the replenishment fluid pump PC functions as a valve that stops and closes the replenishment fluid line LC.

When receiving an instruction for priming execution from the operator, first, the control part performs, as the priming processing, third priming processing for feeding the priming fluid in a flow along arrows C. Thereafter, the control part executes, in order, first priming processing for feeding the priming fluid in a flow along arrows A and second priming processing for feeding the priming fluid in a flow along arrows B.

In the third priming processing, the control part opens the replenishment fluid valve VC and normally drives the replenishment fluid pump PC and reversely drives the blood pump PB. At this time, replenishment fluid or saline functioning as the priming fluid is filled into the fluid container 22. The replenishment fluid pump PC is normally driven, whereby the priming fluid (the replenishment fluid or the saline) filled into the fluid container 22 flows in the order of the replenishment fluid line LC, the venous side line LV, the hemodialysis filter 110b, the arterial side line LA, and the discharging part 14. Consequently, the replenishment fluid line LC is filled with the priming fluid. Air remaining in the replenishment fluid line LC is eliminated. After the third priming processing, the control part closes the replenishment valve VC in order to execute the first and second priming processing. Content of the first and second priming processing executed thereafter is the same as the content explained above. Therefore, explanation of the content is omitted.

Figure 14:
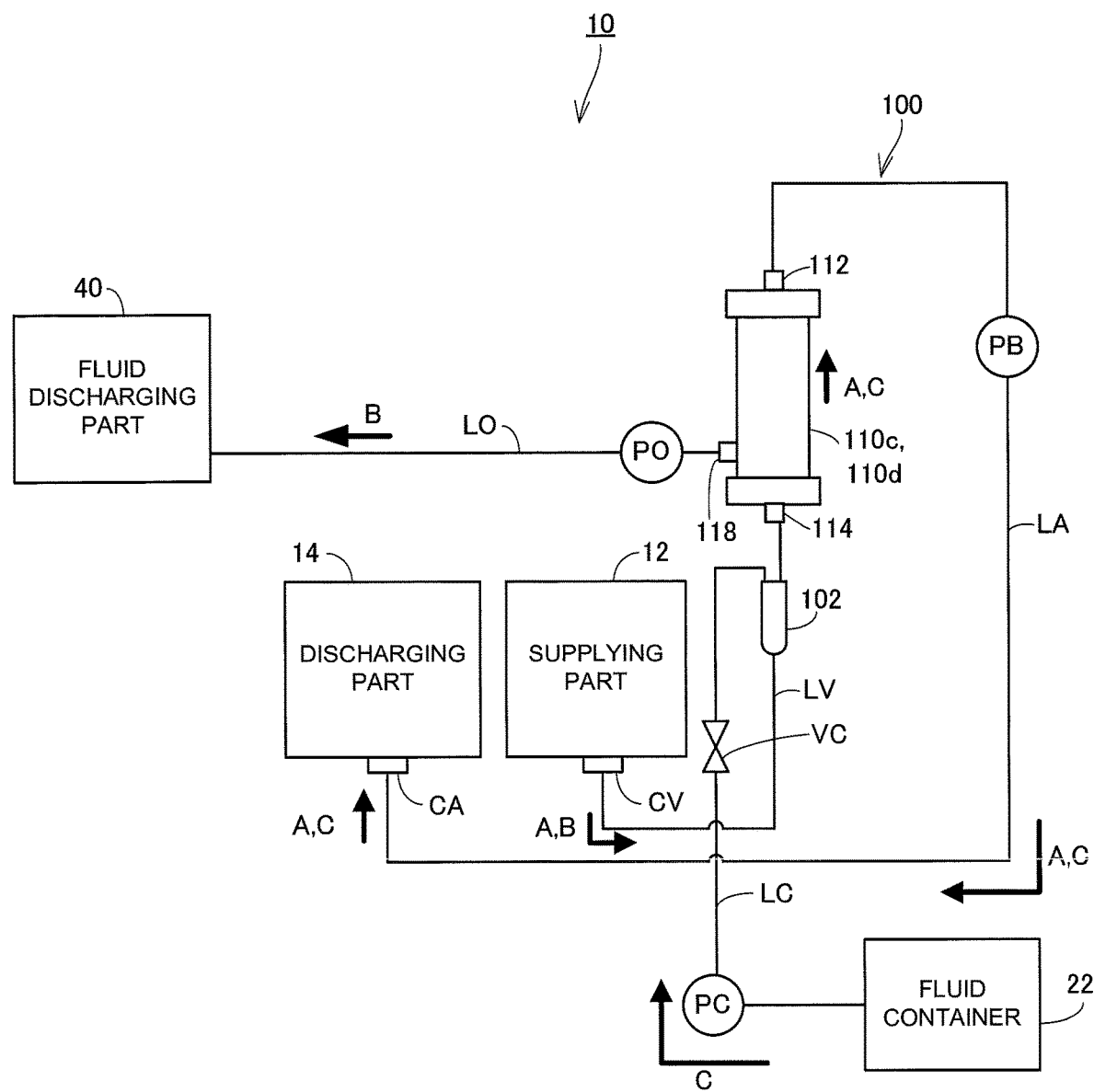
FIG. 14 is a diagram showing the configuration of a blood purification device in a tenth embodiment of the present invention.

A tenth embodiment will be explained. FIG. 14 is a diagram showing the configuration of the blood purification device 10 in the tenth embodiment. This blood purification device 10 has a configuration particularly suitable to executing hemofiltration or plasmapheresis. In this case, as the blood purifier 110, the blood filter (the hemofilter) 110c, on the inside of which the hollow fiber membrane is provided, or the plasma separator 110d is used. In the blood circuit 100, the replenishment fluid line LC for replenishing components lost in the process of the blood purification (the hemofiltration or the plasma separation) is provided. The fluid container 22 filled with the replenishment fluid or the priming fluid is connected to one end of the replenishment fluid line LC.

The blood purification device 10 does not perform supply and discharge of the dialysis fluid and collects and discards filtrate discharged in the hemofiltration or a plasma component separated in the plasmapheresis. Therefore, the blood purification device 10 does not include the lead-in line LI and the lead-in pump PI and includes only the lead-out line LO and the lead-out pump PO. A fluid discharging part 40 from which discharged fluid is discharged is provided at the distal end of the lead-out line LO. This fluid discharging part 40 functions as a second discharging part from which the priming fluid is discharged. If instructed by the operator to execute priming, the control part executes third priming processing (arrows C in FIG. 14), first priming processing (arrows A in FIG. 14), and second priming processing (arrows B in FIG. 14).

As is evident from the above explanation, the control part is provided that, in a state in which the supplying part that supplies the priming fluid and the venous side line LV are connected, and the discharging part from which the priming fluid after use is discharged and the arterial side line LA are connected, when receiving an instruction for priming execution, drives the blood pump PB and executes the first priming processing for priming the blood circuit 100 and the blood purifier 110. Then, it is possible to appropriately perform the priming processing without providing an unnecessary branch line on the blood circuit 100 side. Note that in FIG. 11 to FIG. 14, the supplying part 12 and the discharging part 14 are described as separate containers. However, as shown in FIG. 10, one container (the priming fluid container 30) may be used as a supplying part and a discharging part.

REFERENCE SIGNS LIST 10 blood purification device
12 supplying part 14 discharging part
16 control part
20 dialysis fluid supplying and discharging device
22 fluid container
24, 28 priming-fluid discharging part
26 priming-fluid supplying part
32 dialysis fluid tank
34 dialysis fluid reproduction column
36 replenishment line
40 fluid discharging part
100 blood circuit
102 air trap chamber
110 blood purifier
110a dialyzer
110b hemodialysis filter (hemodiafilter)
110c blood filter (hemofilter)
110d plasma separator
110e blood purification column
112 blood inlet
114 blood outlet
118 lead-in port
119 lead-out port
130 puncture needle
CA arterial side connector
CD discharge connector
CS supply connector
CV venous side connector
LA arterial side line
LC replenishment fluid line
LD discharge line
LI lead-in line
LO lead-out line
LS supply line
LV venous side line
PB blood pump
PC replenishment fluid pump
PI lead-in pump
PO lead-out pump
VC replenishment fluid valve
VI lead-in valve
VS supply valve

The invention claimed is:

1. A blood purification device used with a blood circuit, which includes an arterial side line and a venous side line, and a blood purifier attached thereto, the arterial side line and the venous side line being connected to a respective end of the blood purifier, the blood purification device comprising:
a supply line connected to a supplying part that is configured to supply priming fluid, the supply line being connectable to a distal end of the venous side line;
a discharge line connected to a discharging part that is configured to discharge the priming fluid after use, the discharge line including:
a distal end having a connector that is configured to detachably connect to a distal end of the arterial side line; and
a proximal end that is joined midway in a lead-out line that connects the discharging part and the blood purifier such that the discharge line is branched from the lead-out line at a position in between the discharging part and the blood purifier; and
a blood pump provided midway in the arterial side line, wherein
in a state in which the supply line and the venous side line are connected, and the discharge line and the arterial side line are connected, the blood purification device is configured to execute a first priming process and a second priming process to prime the blood circuit and the blood purifier; in the first priming process, the blood purification device is configured to drive the blood pump to prime the blood circuit and the blood purifier such that the priming fluid flows axially through the blood purifier, and in the second priming process, the blood purification device is configured feed the priming fluid between the supplying part, the blood purifier, and the discharging part through a lead-in line that connects the supplying part and the blood purifier and through the lead-out line such that the priming fluid flows through at least one port that is disposed on a circumferential surface of the blood purifier and is coupled to one of the lead-in line and the lead-out line.

2. The blood purification device according to claim 1, wherein during the first priming process, the blood pump is configured to be reversely driven to deliver the priming fluid in a direction opposite to a direction of fluid flow during execution of a blood purifying method.

3. The blood purification device according to claim 1, wherein:
the blood purifier is a dialyzer,
the discharging part is a dialysis fluid discharge device that is configured to discharge dialysis fluid from the dialyzer.

4. The blood purification device according to claim 1, wherein the supply line is a line branching midway in the lead-in line that connects the supplying part and the blood purifier.

5. The blood purification device according to claim 4, wherein:
the blood purifier is a dialyzer,
the supplying part is a dialysis fluid supply device that is configured to supply dialysis fluid to the dialyzer.

6. The blood purification device according to claim 5 further comprising:
a lead-in pump that is provided midway in the lead-in line and is configured to send the dialysis fluid supplied from the dialysis fluid supply device to the dialyzer;
a lead-out pump that is provided midway in the lead-out line and is configured to send fluid discharged from the dialyzer to the discharging part; and
a switching mechanism including a valve, the switching mechanism being configured to switch a supply destination of the dialysis fluid supplied from the dialysis fluid supply device to the supply line or the dialyzer, wherein
in the first priming process, the blood purification device is configured to drive the blood pump in a state in which the supply destination of the dialysis fluid is switched to the supply line, and
in the second priming process, the blood purification device is configured to drive the lead-in pump and the lead-out pump in a state in which the supply destination of the dialysis fluid is switched to the blood purifier.

7. The blood purification device according to claim 6, wherein, in the second priming process, the lead-in pump and the lead-out pump are configured to be normally driven such that a direction of fluid flow is the same as a direction of fluid flow during execution of a blood purifying method.

8. The blood purification device according to claim 3, wherein the priming fluid is dialysis fluid.

9. The blood purification device according to claim 1, wherein the supplying part is a priming fluid container filled with the priming fluid or a line connected to a supply source of the priming fluid provided on an outside of the blood purification device.

10. The blood purification device according to claim 1, wherein the discharging part is a discharge fluid container filled with used priming fluid or a line connected to a discarding part of the priming fluid provided on an outside of the blood purification device.

11. The blood purification device according to claim 1, wherein:
   the blood circuit further includes a replenishment fluid line that is connected midway in at least one line of the venous side line and the arterial side line and is configured to guide fluid to be replenished to the at least one line,
   the blood purification device further includes a replenishment fluid pump that is provided midway in the at least one line and is configured to send the fluid to be replenished to the at least one line, and
   the blood purification device is configured to drive the replenishment fluid pump to prime the replenishment fluid line.

12. A priming method for discharging air from a blood circuit including an arterial side line, a venous side line, and a blood purifier, the arterial side line and the venous side line being connected to a respective end of the blood purifier, the priming method comprising:
   connecting a distal end of the venous side line to a supply line that is connected to a supplying part that is configured to supply priming fluid;
   connecting a distal end of the arterial side line to a connector disposed on a distal end of a discharge line, the discharge line being connected to a discharging part that is configured to discharge the priming fluid after use, the discharge line including a proximal end that is joined midway in a lead-out line that connects the discharging part and the blood purifier such that the discharge line is branched from the lead-out line at a position in between the discharging part and the blood purifier; and
   priming the blood circuit and the blood purifier via a first priming process and a second priming process in a state in which the supply line and the venous side line are connected, and the discharge line and the arterial side line are connected, the first priming process comprising driving a blood pump provided midway in the arterial side line and feeding the priming fluid to the blood circuit and the blood purifier such that the priming fluid flows axially through the blood purifier, and the second priming process comprising feeding the priming fluid between the supplying part, the blood purifier, and the discharging part through a lead-in line that connects the supplying part and the blood purifier and through the lead-out line such that the priming fluid flows through at least one port that is disposed on a circumferential surface of the blood purifier and is coupled to one of the lead-in line and the lead-out line.

13. A blood purification device used with a blood circuit, which includes an arterial side line and a venous side line, and a blood purifier attached thereto, the arterial side line and the venous side line being connected to a respective end of the blood purifier, the blood purification device comprising:
   a blood pump provided midway in the arterial side line;
   a controller that is configured to control at least driving of the blood pump;
   a discharging part;
   a lead-in line that connects the discharging part and the blood purifier;
   a lead-out line that connects the discharging part and the blood purifier;
   a lead-in pump provided midway in the lead-in line;
   a lead-out pump provided midway in the lead-out line;
   a dialysis fluid reproduction column provided midway in the lead-out line, wherein:
   in a state in which a venous side connector provided at a distal end of the venous side line is directly connected to a supplying part that is configured to supply priming fluid, and an arterial side connector provided at a distal end of the arterial side line is directly connected to a second discharging part that is configured to discharge the priming fluid after use, the controller is configured to drive the blood pump and execute a first priming processing for priming the blood circuit and the blood purifier when receiving instruction for priming execution, and
   after the first priming processing, the controller is configured to drive the lead-in pump and the lead-out pump and execute a second priming processing for feeding the priming fluid to the lead-in line and the lead-out line such that the priming fluid is fed to the dialysis fluid reproduction column.

14. The blood purification device according to claim 13, wherein, in the first priming processing, the controller is configured to reversely drive the blood pump to deliver the priming fluid in a direction opposite to a direction of fluid flow during execution of a blood purifying method.

15. The blood purification device according to claim 13, wherein, in the second priming processing, the controller is configured to normally drive the lead-out pump to deliver the priming fluid in the same direction as a direction of fluid flow during execution of a blood purifying method.

16. The blood purification device according to claim 13, wherein, in the second priming processing, the controller is configured to reversely drive the lead-in pump to deliver the priming fluid in a direction opposite to a direction of fluid flow during execution of a blood purifying method.

17. The blood purification device according to claim 13, wherein the discharging part is a dialysis fluid tank that is configured to store dialysis fluid.

18. The blood purification device according to claim 13, wherein one container is used as the supply part and the second discharging part.

19. The blood purification device according to claim 13, wherein, during the second priming processing, the controller is configured to drive the lead-in pump and the lead-out pump to feed the priming fluid to the lead-in line and the lead-out line such that the priming fluid flows from the blood purifier into at least one of the lead-out line and the lead-in line and into the discharging part in a state in which the blood pump is not driven.

20. The blood purification device according to claim 1, wherein the supply line includes:
   a distal end having a connector that is configured to detachably connect to a distal end of the venous side line, and
   a proximal end that is joined midway in the lead-in line such that the supply line is branched from the lead-in line at a position in between the supplying part and the blood purifier.

* * * * *